(12) United States Patent
Thorne, Jr. et al.

(10) Patent No.: US 7,998,106 B2
(45) Date of Patent: Aug. 16, 2011

(54) SAFETY DISPENSING SYSTEM FOR HAZARDOUS SUBSTANCES

(76) Inventors: Gale H. Thorne, Jr., Bountiful, UT (US); Gale H. Thorne, Bountiful, UT (US)

( * ) Notice: Subject to any disclaimer, the term of this patent is extended or adjusted under 35 U.S.C. 154(b) by 0 days.

(21) Appl. No.: 11/446,779

(22) Filed: Jun. 5, 2006

(65) Prior Publication Data

US 2006/0224105 A1 Oct. 5, 2006

Related U.S. Application Data

(63) Continuation-in-part of application No. 11/359,304, filed on Feb. 21, 2006, now Pat. No. 7,101,354, which is a continuation-in-part of application No. 11/284,504, filed on Nov. 22, 2005, now Pat. No. 7,048,720, which is a continuation-in-part of application No. 10/838,101, filed on May 3, 2004, now Pat. No. 6,997,910.

(51) Int. Cl.
*A61M 1/00* (2006.01)
*A61M 5/00* (2006.01)

(52) U.S. Cl. .......................................... 604/32; 604/191

(58) Field of Classification Search .................... 604/32, 604/82–92, 174, 177, 180, 191, 212–217
See application file for complete search history.

(56) References Cited

U.S. PATENT DOCUMENTS

| | | | |
|---|---|---|---|
| 2,564,977 A * | 8/1951 | Hu | 604/32 |
| 3,859,985 A * | 1/1975 | Eckhart | 251/344 |
| 3,946,732 A | 3/1976 | Hurscham | |
| 3,976,068 A * | 8/1976 | Lundquist | 604/518 |
| 4,014,330 A | 3/1977 | Genese | |
| 4,014,332 A | 3/1977 | Sneider | |
| 4,031,892 A | 6/1977 | Hurschman | |
| 4,031,895 A | 6/1977 | Porter | |
| 4,036,225 A | 7/1977 | Maury | |
| 4,041,945 A | 8/1977 | Guiney | |
| 4,048,999 A | 9/1977 | Köbel | |
| 4,055,177 A | 10/1977 | Cohen | |
| 4,061,144 A | 12/1977 | Strickman et al. | |
| 4,066,080 A | 1/1978 | Sneider | |
| 4,085,749 A | 4/1978 | Chambron | |
| 4,116,240 A | 9/1978 | Guiney | |
| 4,133,313 A | 1/1979 | Sneider | |
| 4,153,057 A | 5/1979 | Köbel | |
| 4,159,570 A | 7/1979 | Baskas et al. | |
| 4,180,070 A | 12/1979 | Genese | |
| 4,180,072 A * | 12/1979 | Sneider | 604/32 |

(Continued)

FOREIGN PATENT DOCUMENTS

EP 0 028 557 5/1981

(Continued)

OTHER PUBLICATIONS

Brochure item: Published by tyco/Healthcare of KENDALL-LTP in the United States (undated) describing a Vial Venting system product called ChemoBloc Vial Venting system.

(Continued)

*Primary Examiner* — Theodore J Stigell
*Assistant Examiner* — Michael J Anderson

(57) ABSTRACT

A combination of a valve assembly and multi-chamber, sequential delivery syringe is disclosed. The combination effectively provides a safety system for transferring hazardous materials from a vial to a site of use. All potentially hazardous materials are flushed from exposed connecting sites prior to disconnections.

23 Claims, 14 Drawing Sheets

U.S. PATENT DOCUMENTS

| | | | |
|---|---|---|---|
| 4,185,628 A | 1/1980 | Kopfer | |
| 4,210,142 A | 7/1980 | Wörder | |
| 4,254,768 A | 3/1981 | Ty | |
| 4,296,785 A * | 10/1981 | Vitello et al. | 141/105 |
| 4,303,070 A | 12/1981 | Ichikawa et al. | |
| 4,323,066 A | 4/1982 | Bourdon | |
| 4,328,802 A | 5/1982 | Curley et al. | |
| 4,331,146 A | 5/1982 | Brignola | |
| 4,354,507 A | 10/1982 | Raitto | |
| 4,356,822 A | 11/1982 | Winstead-Hall | |
| 4,401,432 A | 8/1983 | Schwartz | |
| 4,405,317 A | 9/1983 | Case | |
| 4,411,275 A | 10/1983 | Raitto | |
| 4,412,836 A | 11/1983 | Brignola | |
| 4,464,173 A | 8/1984 | Tartaglia | |
| 4,464,174 A | 8/1984 | Ennis | |
| 4,479,578 A | 10/1984 | Brignola et al. | |
| 4,515,586 A | 5/1985 | Mendenhall et al. | |
| 4,532,969 A * | 8/1985 | Kwaan | 141/27 |
| 4,540,410 A | 9/1985 | Wood et al. | |
| 4,543,094 A | 9/1985 | Barnwell | |
| 4,564,054 A * | 1/1986 | Gustavsson | 141/329 |
| 4,576,211 A * | 3/1986 | Valentini et al. | 141/329 |
| 4,581,015 A | 4/1986 | Alfano | |
| 4,589,871 A | 5/1986 | Imbert | |
| 4,594,073 A | 6/1986 | Stine | |
| 4,610,666 A | 9/1986 | Pizzino | |
| 4,643,721 A * | 2/1987 | Brunet | 604/191 |
| 4,655,747 A | 4/1987 | Allen, Jr. | |
| 4,668,223 A | 5/1987 | Grotenhuis | |
| 4,673,396 A | 6/1987 | Urbaniak | |
| 4,693,706 A | 9/1987 | Ennis, III | |
| 4,698,055 A | 10/1987 | Sealfon | |
| 4,722,733 A * | 2/1988 | Howson | 604/411 |
| 4,737,150 A | 4/1988 | Baeumle et al. | |
| 4,738,660 A | 4/1988 | Lucas | |
| 4,768,568 A * | 9/1988 | Fournier et al. | 141/286 |
| 4,773,900 A | 9/1988 | Cochran | |
| 4,776,704 A | 10/1988 | Kopunek et al. | |
| 4,792,329 A * | 12/1988 | Schreuder | 604/90 |
| 4,833,329 A * | 5/1989 | Quint et al. | 250/432 PD |
| 4,834,149 A * | 5/1989 | Fournier et al. | 141/1 |
| 4,853,546 A * | 8/1989 | Abe et al. | 250/432 PD |
| 4,857,056 A * | 8/1989 | Talonn | 604/135 |
| 4,861,335 A | 8/1989 | Reynolds | |
| 4,874,381 A | 10/1989 | Vetter | |
| 4,929,230 A | 5/1990 | Pfleger | |
| 4,932,937 A * | 6/1990 | Gustavsson et al. | 604/87 |
| 4,932,944 A * | 6/1990 | Jagger et al. | 604/191 |
| 4,936,841 A * | 6/1990 | Aoki et al. | 604/413 |
| 4,938,063 A * | 7/1990 | Leighley | 73/40.7 |
| 4,968,299 A | 11/1990 | Ahlstrand et al. | |
| 4,979,652 A | 12/1990 | Saulle | |
| 4,986,818 A | 1/1991 | Imbert et al. | |
| 5,012,845 A * | 5/1991 | Averette | 141/329 |
| 5,026,353 A | 6/1991 | Bartman | |
| 5,032,117 A | 7/1991 | Motta | |
| 5,037,390 A * | 8/1991 | Raines et al. | 604/83 |
| 5,037,402 A | 8/1991 | Bartman | |
| 5,039,863 A * | 8/1991 | Matsuno et al. | 250/432 PD |
| 5,061,252 A | 10/1991 | Dragosits | |
| 5,062,828 A | 11/1991 | Waltz | |
| 5,069,670 A | 12/1991 | Vetter et al. | |
| 5,080,649 A | 1/1992 | Vetter | |
| 5,109,160 A * | 4/1992 | Evers | 250/432 PD |
| 5,122,117 A | 6/1992 | Haber et al. | |
| 5,137,511 A | 8/1992 | Reynolds | |
| 5,139,490 A | 8/1992 | Vetter et al. | |
| 5,147,324 A * | 9/1992 | Skakoon et al. | 604/192 |
| 5,171,220 A | 12/1992 | Morimoto | |
| 5,185,007 A * | 2/1993 | Middaugh et al. | 604/320 |
| 5,213,236 A | 5/1993 | Brown et al. | |
| 5,236,420 A | 8/1993 | Pfleger | |
| 5,271,531 A | 12/1993 | Rohr et al. | |
| 5,286,257 A | 2/1994 | Fischer | |
| 5,290,228 A | 3/1994 | Uemura et al. | |
| 5,290,259 A | 3/1994 | Fischer | |
| 5,298,024 A | 3/1994 | Richmond | |
| 5,304,137 A | 4/1994 | Fluke | |
| 5,308,322 A * | 5/1994 | Tennican et al. | 604/83 |
| 5,312,336 A | 5/1994 | Haber et al. | |
| 5,329,976 A | 7/1994 | Haber et al. | |
| 5,330,426 A | 7/1994 | Kriesel et al. | |
| 5,338,303 A | 8/1994 | King et al. | |
| 5,354,285 A | 10/1994 | Mazurik et al. | |
| 5,360,410 A | 11/1994 | Wacks | |
| 5,364,369 A | 11/1994 | Reynolds | |
| 5,372,586 A | 12/1994 | Haber et al. | |
| RE34,845 E | 1/1995 | Vetter et al. | |
| 5,395,325 A | 3/1995 | Moreno et al. | |
| 5,395,326 A | 3/1995 | Haber et al. | |
| 5,399,170 A | 3/1995 | Whitley | |
| 5,429,610 A | 7/1995 | Vaillancourt | |
| 5,439,452 A * | 8/1995 | McCarty | 604/248 |
| 5,445,614 A | 8/1995 | Haber et al. | |
| 5,466,219 A * | 11/1995 | Lynn et al. | 604/86 |
| 5,489,266 A | 2/1996 | Gremard | |
| 5,496,284 A | 3/1996 | Waldenburg | |
| 5,496,473 A * | 3/1996 | Chow | 210/635 |
| 5,501,371 A | 3/1996 | Schwartz-Feldman | |
| 5,522,804 A | 6/1996 | Lynn | |
| 5,531,683 A | 7/1996 | Kriesel et al. | |
| 5,542,760 A | 8/1996 | Chanoch et al. | |
| 5,542,934 A | 8/1996 | Silver | |
| 5,549,569 A * | 8/1996 | Lynn et al. | 604/191 |
| 5,566,729 A * | 10/1996 | Grabenkort et al. | 141/25 |
| 5,599,312 A | 2/1997 | Higashikawa | |
| 5,605,542 A | 2/1997 | Tanaka et al. | |
| 5,630,800 A | 5/1997 | Blank et al. | |
| 5,637,087 A | 6/1997 | O'Neil et al. | |
| 5,643,218 A * | 7/1997 | Lynn et al. | 604/191 |
| 5,647,845 A * | 7/1997 | Haber et al. | 604/32 |
| 5,665,068 A | 9/1997 | Takamura | |
| 5,674,195 A | 10/1997 | Truthan | |
| 5,685,846 A | 11/1997 | Michaels, Jr. | |
| 5,688,252 A | 11/1997 | Matsuda et al. | |
| 5,695,465 A | 12/1997 | Zhu | |
| 5,704,520 A | 1/1998 | Gross | |
| 5,704,918 A * | 1/1998 | Higashikawa | 604/191 |
| 5,713,857 A | 2/1998 | Grimard et al. | |
| 5,716,339 A | 2/1998 | Tanaka et al. | |
| 5,743,886 A * | 4/1998 | Lynn et al. | 604/191 |
| 5,743,890 A | 4/1998 | Hjertman et al. | |
| 5,766,147 A | 6/1998 | Sancpff et al. | |
| 5,779,668 A | 7/1998 | Grabenkort | |
| 5,785,682 A | 7/1998 | Grabenkort | |
| 5,788,670 A | 8/1998 | Reinhard et al. | |
| 5,795,337 A | 8/1998 | Grimard | |
| 5,807,323 A | 9/1998 | Kriesel et al. | |
| 5,817,056 A | 10/1998 | Tanaka et al. | |
| 5,817,955 A | 10/1998 | Gherson et al. | |
| 5,819,988 A | 10/1998 | Sawhney et al. | |
| 5,827,233 A | 10/1998 | Futagawa et al. | |
| 5,827,262 A | 10/1998 | Neftel et al. | |
| 5,830,193 A * | 11/1998 | Higashikawa | 604/191 |
| 5,851,200 A * | 12/1998 | Higashikawa et al. | 604/199 |
| 5,860,739 A | 1/1999 | Cannon | |
| 5,865,798 A | 2/1999 | Grimard et al. | |
| 5,865,799 A | 2/1999 | Tanaka et al. | |
| 5,876,372 A | 3/1999 | Grabenkort et al. | |
| 5,891,087 A | 4/1999 | Ohtani et al. | |
| 5,899,881 A | 5/1999 | Grimard et al. | |
| 5,899,889 A | 5/1999 | Futagawa et al. | |
| 5,971,181 A | 10/1999 | Niedospial, Jr. et al. | |
| 5,971,953 A | 10/1999 | Bachynsky | |
| 5,993,744 A * | 11/1999 | Rao et al. | 422/103 |
| 5,998,217 A * | 12/1999 | Rao et al. | 436/179 |
| 6,027,472 A | 2/2000 | Kriesel et al. | |
| 6,027,481 A | 2/2000 | Barrelle et al. | |
| 6,040,186 A * | 3/2000 | Lewis et al. | 436/53 |
| 6,045,004 A | 4/2000 | Elliott | |
| 6,056,921 A * | 5/2000 | Rao et al. | 422/65 |
| 6,065,645 A | 5/2000 | Sawhney et al. | |
| 6,070,761 A * | 6/2000 | Bloom et al. | 222/81 |
| 6,077,252 A | 6/2000 | Siegel | |
| 6,090,081 A | 7/2000 | Sudo et al. | |
| 6,120,478 A | 9/2000 | Moore et al. | |

| Patent/Pub No. | Date | Name | Ref |
|---|---|---|---|
| 6,123,685 A | 9/2000 | Reynolds | |
| 6,132,400 A | 10/2000 | Waldenburg | |
| 6,142,977 A | 11/2000 | Kolberg et al. | |
| 6,143,573 A * | 11/2000 | Rao et al. | 436/180 |
| 6,149,628 A | 11/2000 | Szapiro et al. | |
| 6,157,036 A * | 12/2000 | Whiting et al. | 250/432 PD |
| 6,161,364 A | 12/2000 | Kolberg | |
| 6,164,144 A * | 12/2000 | Berg | 73/863.21 |
| 6,171,220 B1 | 1/2001 | Lumpkin | |
| 6,196,016 B1 * | 3/2001 | Knowles et al. | 62/292 |
| 6,210,361 B1 * | 4/2001 | Kamen et al. | 604/82 |
| 6,224,561 B1 * | 5/2001 | Swendson et al. | 600/562 |
| 6,224,568 B1 | 5/2001 | Morimoto et al. | |
| 6,234,190 B1 | 5/2001 | Fisher et al. | |
| 6,234,997 B1 * | 5/2001 | Kamen et al. | 604/131 |
| 6,245,046 B1 | 6/2001 | Sibbitt | |
| 6,253,804 B1 * | 7/2001 | Safabash | 141/97 |
| 6,267,154 B1 | 7/2001 | Felicelli et al. | |
| 6,290,680 B1 | 9/2001 | Forsberg et al. | |
| 6,343,629 B1 * | 2/2002 | Wessman et al. | 141/383 |
| 6,368,306 B1 | 4/2002 | Koska | |
| 6,379,328 B1 | 4/2002 | Mac Clay | |
| 6,394,314 B1 | 5/2002 | Sawhney et al. | |
| H2027 H | 6/2002 | Brown et al. | |
| 6,398,031 B1 | 6/2002 | Frezza | |
| 6,402,716 B1 | 6/2002 | Ryoo et al. | |
| 6,408,897 B1 * | 6/2002 | Laurent et al. | 141/100 |
| 6,409,708 B1 * | 6/2002 | Wessman | 604/284 |
| 6,419,656 B1 | 7/2002 | Vetter et al. | |
| 6,425,880 B1 | 7/2002 | Marshall | |
| 6,425,885 B1 | 7/2002 | Fischer et al. | |
| 6,464,667 B1 * | 10/2002 | Kamen et al. | 604/131 |
| 6,468,250 B2 | 10/2002 | Yang | |
| 6,474,375 B2 * | 11/2002 | Spero et al. | 141/329 |
| 6,527,019 B2 * | 3/2003 | Laurent et al. | 141/100 |
| 6,537,263 B1 * | 3/2003 | Aneas | 604/412 |
| 6,544,233 B1 * | 4/2003 | Fukui et al. | 604/191 |
| 6,564,972 B2 | 5/2003 | Sawhney et al. | |
| 6,591,876 B2 * | 7/2003 | Safabash | 141/329 |
| 6,602,223 B2 | 8/2003 | Szapiro et al. | |
| 6,622,721 B2 | 9/2003 | Vedrine et al. | |
| 6,641,561 B1 | 11/2003 | Hill et al. | |
| 6,645,179 B1 | 11/2003 | Ishikawa et al. | |
| 6,692,468 B1 | 2/2004 | Waldenburg | |
| 6,698,622 B2 | 3/2004 | Sawhney et al. | |
| 6,715,520 B2 * | 4/2004 | Andreasson et al. | 141/329 |
| 6,723,074 B1 | 4/2004 | Halseth | |
| 6,740,062 B2 | 5/2004 | Hjertman | |
| 6,807,797 B2 | 10/2004 | Forsberg et al. | |
| 6,817,987 B2 | 11/2004 | Vetter et al. | |
| 6,866,653 B2 * | 3/2005 | Bae | 604/191 |
| 6,884,231 B1 | 4/2005 | Walters et al. | |
| 6,929,126 B1 | 8/2005 | Herbert | |
| 6,948,522 B2 * | 9/2005 | Newbrough et al. | 137/550 |
| 6,962,576 B2 | 11/2005 | Sibbitt | |
| 6,972,005 B2 | 12/2005 | Boehm, Jr. et al. | |
| 6,997,910 B2 * | 2/2006 | Howlett et al. | 604/191 |
| 7,001,362 B2 | 2/2006 | Vincent | |
| 7,033,339 B1 * | 4/2006 | Lynn | 604/256 |
| 7,048,720 B1 * | 5/2006 | Thorne et al. | 604/191 |
| 7,077,826 B1 | 7/2006 | Gray | |
| 7,081,107 B2 | 7/2006 | Kito et al. | |
| 7,101,354 B2 * | 9/2006 | Thorne et al. | 604/191 |
| 7,164,133 B2 | 1/2007 | Hjertman et al. | |
| 7,198,619 B2 | 4/2007 | Bills et al. | |
| 7,267,668 B2 | 9/2007 | Ruben | |
| 2001/0008962 A1 | 7/2001 | Forsberg et al. | |
| 2001/0009989 A1 | 7/2001 | Sibbitt | |
| 2001/0031948 A1 * | 10/2001 | Cruise et al. | 604/191 |
| 2001/0034506 A1 | 10/2001 | Hirschman et al. | |
| 2002/0017196 A1 | 2/2002 | Lichon et al. | |
| 2002/0022804 A1 | 2/2002 | Connolly et al. | |
| 2002/0035351 A1 | 3/2002 | Lodice | |
| 2002/0055708 A1 | 5/2002 | Peterson | |
| 2002/0065490 A1 | 5/2002 | Heinz et al. | |
| 2002/0082560 A1 | 6/2002 | Yang | |
| 2002/0145007 A1 | 10/2002 | Sawhney et al. | |
| 2002/0192113 A1 * | 12/2002 | Uffenheimer et al. | 422/67 |
| 2003/0004467 A1 | 1/2003 | Musick et al. | |
| 2003/0036724 A1 | 2/2003 | Vetter et al. | |
| 2003/0040701 A1 | 2/2003 | Dalmose | |
| 2003/0088216 A1 | 5/2003 | Py | |
| 2003/0105433 A1 | 6/2003 | Ruben | |
| 2003/0105477 A1 | 6/2003 | Schwartz et al. | |
| 2003/0167041 A1 | 9/2003 | Rosoff et al. | |
| 2003/0195489 A1 | 10/2003 | Peterson | |
| 2003/0197024 A1 | 10/2003 | Sawhney et al. | |
| 2003/0199816 A1 | 10/2003 | Ramming | |
| 2003/0212372 A1 | 11/2003 | Bills et al. | |
| 2004/0006315 A1 | 1/2004 | Lo | |
| 2004/0039344 A1 * | 2/2004 | Baldwin et al. | 604/209 |
| 2004/0064041 A1 | 4/2004 | Lazzaro et al. | |
| 2004/0092864 A1 | 5/2004 | Boehm, Jr. et al. | |
| 2004/0127846 A1 | 7/2004 | Dunn et al. | |
| 2004/0186437 A1 | 9/2004 | Frenette et al. | |
| 2004/0215135 A1 | 10/2004 | Sheldrake et al. | |
| 2004/0236273 A1 | 11/2004 | Tanaka et al. | |
| 2004/0254525 A1 * | 12/2004 | Uber et al. | 604/67 |
| 2005/0004530 A1 | 1/2005 | Grabenkort et al. | |
| 2005/0028489 A1 | 2/2005 | Forsberg et al. | |
| 2005/0039417 A1 | 2/2005 | Liedtke et al. | |
| 2005/0113754 A1 | 5/2005 | Cowan | |
| 2005/0119609 A1 | 6/2005 | McLean | |
| 2005/0119610 A1 | 6/2005 | Peuker et al. | |
| 2005/0177100 A1 | 8/2005 | Harper et al. | |
| 2005/0182357 A1 | 8/2005 | Snell et al. | |
| 2005/0192543 A1 | 9/2005 | Sibbitt | |
| 2005/0234337 A1 | 10/2005 | Browne | |
| 2005/0236063 A1 | 10/2005 | DiGregorio et al. | |
| 2005/0240159 A1 | 10/2005 | Kito et al. | |
| 2005/0245880 A1 | 11/2005 | Howlett et al. | |
| 2005/0261635 A1 | 11/2005 | Byrne et al. | |
| 2005/0277891 A1 | 12/2005 | Sibbitt | |
| 2006/0052747 A1 | 3/2006 | Nishimura et al. | |
| 2006/0069356 A1 | 3/2006 | Witowski | |
| 2006/0079834 A1 | 4/2006 | Tennican et al. | |
| 2006/0084914 A1 | 4/2006 | Tung | |
| 2006/0100587 A1 | 5/2006 | Bertron et al. | |
| 2006/0100590 A1 | 5/2006 | Thorne, Jr. et al. | |
| 2006/0118199 A1 | 6/2006 | Yamazaki | |
| 2006/0142701 A1 | 6/2006 | Thorne, Jr. et al. | |
| 2006/0184103 A1 | 8/2006 | Paproski et al. | |
| 2006/0189943 A1 | 8/2006 | Kato et al. | |
| 2006/0200084 A1 | 9/2006 | Ito et al. | |
| 2006/0211995 A1 | 9/2006 | Myhrberg et al. | |
| 2006/0224105 A1 * | 10/2006 | Thorne et al. | 604/32 |
| 2006/0258977 A1 | 11/2006 | Lee | |
| 2007/0005020 A1 | 1/2007 | Laveault | |
| 2007/0005022 A1 | 1/2007 | Byrne et al. | |
| 2007/0073226 A1 | 3/2007 | Polidoro et al. | |
| 2007/0156102 A1 | 7/2007 | Py | |
| 2007/0167910 A1 | 7/2007 | Tennican et al. | |
| 2007/0185438 A1 | 8/2007 | Haimi et al. | |
| 2007/0208295 A1 | 9/2007 | Oloodmiyazdi | |
| 2007/0219492 A1 | 9/2007 | Lucas et al. | |
| 2007/0249996 A1 | 10/2007 | Tennican et al. | |
| 2007/0255200 A1 | 11/2007 | McLean et al. | |
| 2007/0255203 A1 | 11/2007 | Tennican et al. | |
| 2007/0260176 A1 | 11/2007 | Tennican et al. | |
| 2007/0265574 A1 | 11/2007 | Tennican et al. | |
| 2007/0265577 A1 | 11/2007 | Uematsu et al. | |
| 2009/0057589 A1 | 3/2009 | Thorne, Jr. et al. | |
| 2009/0062740 A1 | 3/2009 | Thorne, Jr. | |
| 2009/0194453 A1 | 8/2009 | Thorne, Jr. et al. | |
| 2009/0198211 A1 | 8/2009 | Thorne, Jr. et al. | |
| 2009/0198217 A1 | 8/2009 | Thorne, Jr. et al. | |
| 2009/0306621 A1 | 12/2009 | Thorne, Jr. et al. | |

FOREIGN PATENT DOCUMENTS

| | | |
|---|---|---|
| EP | 0 047 744 | 6/1981 |
| EP | 0 071 288 A1 | 7/1982 |
| EP | 0 188 981 | 7/1986 |
| EP | 0 201 611 | 11/1986 |
| EP | 0 212 798 A1 | 3/1987 |
| EP | 0 237 636 A2 | 9/1987 |
| EP | 0 298 067 A1 | 1/1989 |
| EP | 0 328 699 | 8/1989 |
| EP | 0 340 880 A2 | 11/1989 |

| | | |
|---|---|---|
| EP | 0 363 338 A1 | 4/1990 |
| EP | 0 429 052 A1 | 5/1991 |
| EP | 0 440 846 | 8/1991 |
| EP | 0 453 667 A1 | 10/1991 |
| EP | 0 470 977 | 2/1992 |
| EP | 0 511 402 A1 | 11/1992 |
| EP | 0 519 240 A1 | 12/1992 |
| EP | 0 520 618 A2 | 12/1992 |
| EP | 0 540 681 A1 | 5/1993 |
| EP | 0 545 324 A1 | 6/1993 |
| EP | 0 568 321 A2 | 11/1993 |
| EP | 0 574 524 A1 | 12/1993 |
| EP | 0 600 580 A2 | 6/1994 |
| EP | 0 605 541 A1 | 7/1994 |
| EP | 0 616 510 A1 | 9/1994 |
| EP | 0 684 848 A1 | 12/1995 |
| EP | 0 692 272 A1 | 1/1996 |
| EP | 0 695 555 A1 | 2/1996 |
| EP | 0 703 797 A1 | 4/1996 |
| EP | 0 709 106 A2 | 5/1996 |
| EP | 0 717 611 | 6/1996 |
| EP | 0 718 002 A2 | 6/1996 |
| EP | 0 720 857 A1 | 7/1996 |
| EP | 0 728 492 A2 | 8/1996 |
| EP | 0 768 905 A1 | 4/1997 |
| EP | 0 781 567 A2 | 7/1997 |
| EP | 0 793 973 A2 | 9/1997 |
| EP | 0 796 658 A2 | 9/1997 |
| EP | 0 815 886 A2 | 1/1998 |
| EP | 0 878 206 A2 | 11/1998 |
| EP | 0 879 611 A2 | 11/1998 |
| EP | 0 882 441 A2 | 12/1998 |
| EP | 0 925 083 | 6/1999 |
| EP | 0 943 349 A1 | 9/1999 |
| EP | 0 983 099 A2 | 3/2000 |
| EP | 1 011 784 | 6/2000 |
| EP | 1 013 299 A1 | 6/2000 |
| EP | 1 019 120 A1 | 7/2000 |
| EP | 1 066 847 A1 | 1/2001 |
| EP | 1 092 441 A1 | 4/2001 |
| EP | 1 096 963 A1 | 5/2001 |
| EP | 1 365 824 | 12/2003 |
| EP | 1 437 150 A1 | 7/2004 |
| EP | 1 450 881 A2 | 9/2004 |
| EP | 1 487 521 A1 | 12/2004 |
| EP | 1 520 597 A1 | 4/2005 |
| EP | 1 530 978 A1 | 5/2005 |
| EP | 1 553 999 A2 | 7/2005 |
| EP | 1 598 088 A1 | 11/2005 |
| EP | 1 602 415 A1 | 12/2005 |
| EP | 1 613 367 A2 | 1/2006 |
| EP | 1 652 540 A2 | 5/2006 |
| EP | 1 684 822 A2 | 8/2006 |
| EP | 1 698 366 A1 | 9/2006 |
| WO | WO 95/21639 | 8/1995 |
| WO | WO-2004/014533 A1 | 2/2004 |

OTHER PUBLICATIONS

A double sided brochure item: Published by Cardinal Health, Inc. in the United States (undated) describing a "SmartSite Vented Vial Access Device" which partners with a Texium closed male luer for closed system access to drug vials.

A double sided brochure item: Published by Cardinal Health, Inc. in the United States (undated) describing the Texium closed male luer for closed system access mentioned in item #2, above.

Information on Related Patents and Patent Applications, see the section of the accompanying Information Disclosure Statement Letter entitled "Related Patents and Patent Applications" for further information, Jul. 19, 2007.

Debiotech brochure from Internet address www.debiotech.com (accessed May 25, 2004).

"Debioject (ClipnJect)" from www.debiotech.com, pp. 1-3.

Information about Related Patents and Patent Applications, see the section of the accompanying Information Disclosure Statement Letter entitled "Related Patents and Patent Applications" for further information.

* cited by examiner

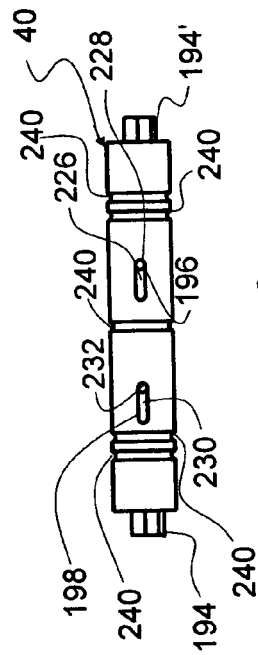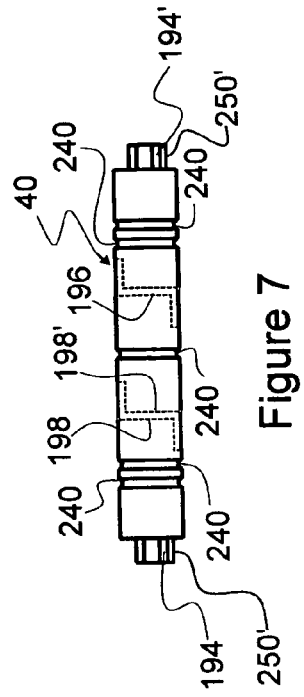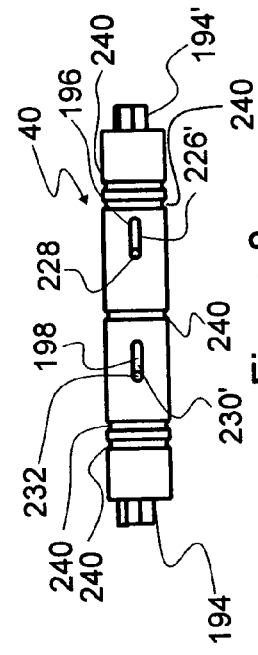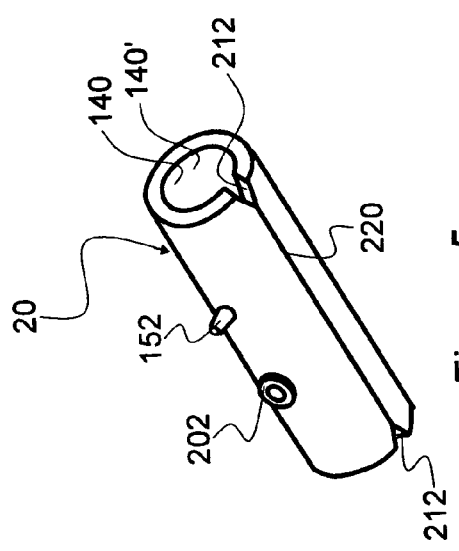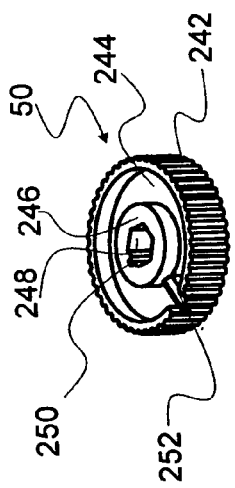

SAFETY DISPENSING SYSTEM FOR HAZARDOUS SUBSTANCES

CONTINUATION-IN-PART

This patent application is a Continuation-in-Part of U.S. patent application Ser. No. 11/359,304, entitled MIXING SYRINGE WITH AND WITHOUT FLUSH [Thorne, Jr. '304], filed on Feb. 21, 2006, and issued as U.S. Pat. No. 7,101,354; which is a Continuation-in-Part of U.S. patent application Ser. No. 11/284,504, entitled MULTI-CHAMBER, SEQUENTIAL DOSE DISPENSING SYRINGE [Thorne, Jr. '504], filed on Nov. 22, 2005, and issued as U.S. Pat. No. 7,048,720; which is a Continuation-in-Part of U.S. patent application Ser. No. 10/838,101, entitled MULTI-CHAMBER, SEQUENTIAL DOSE DISPENSING SYRINGE [Howlett], filed on May 3, 2004, and issued as U.S. Pat. No. 6,997,910; all of which are incorporated herein by reference in their entireties.

FIELD OF INVENTION

This invention is related to safety dispensing systems and, in particular, to dispensing systems which are used to transfer those vial-transported-medicines, which, by their very nature, are considered caustic and dangerous when disposed in direct contact in liquid, or evaporated form, with skin or other body parts, and are generally drawn from the medicine containing vial and transferred to a syringe prior to delivery at a patient site.

DESCRIPTION OF RELATED ART

For many medicines, it is not enough that fluids be transferred from a vial to a syringe aseptically. There are classes of medical fluids which are so caustic and hazardous that any exposure to a handling medical technician or other affected person could have serious negative consequences. Examples of such medical fluids are antiviral drugs, cytotoxins and radio-pharmaceuticals. A U.S. Pat. No. 6,715,520 B2 issued to Kjell Andréasson et al. Feb. 5, 2002 and titled METHOD AND ASSEMBLY FOR FLUID TRANSFER (Andréasson) discloses that insufficient protection is afforded by safety boxes (e.g. laminar flow hoods) due to evaporation and inability to filter out so produced dangerous gases. As well, trapped aerosols in filters make so contaminated filters dangerous to handle.

Also disclosed in Andréasson is concern that unprotected piercing of a vial membrane by a hollow needle may produce an aperture which permits hazardous substances to escape into the surrounding environment. For these reasons, Andréasson teaches a bottle connector and a drug bottle which reduces risk of hazardous leakage. However, further analysis of methods associated with Andréasson makes apparent that even an unprotected connecting element, such as a luer fitting associated with a delivery syringe provides potential for a considerable hazard.

Definition of Terms:

Following is a brief list of clarifying definitions for terms used in this Application:

assembly n: a device which is made from at least two interconnected parts barrel n: a cylindrical elongated portion of a syringe which is conventionally open on one end to receive a plunger and stem used for displacing fluid within the barrel and partially closed at an opposite end except for an orifice through which fluid is ejected or aspirated bi-stable adj: a descriptor for a device having two stable states clinch n: a structure or device which acts upon a part to clamp it closed while in contact therewith conventional adj: sanctioned by general custom; i.e. commonplace, ordinary chamber n: a volumetric portion of a divided barrel disparate n: when used in conjunction with a liquid or fluid volume, a volume of liquid which is distinctly separate from another liquid volume differential pressure ($\Delta P$) n: a pressure gradient resulting from unequal pressures exerted upon opposing sides of a structure; generally as used herein, $\Delta P = P_p - P_d$ distal adj: a term which depicts placement away from a reference point (e.g. away from a user of a syringe)

dome n: an arcuately shaped surface (e.g. a hemisphere)

downstream adj: a direction which is consistent with flow out of a syringe or away from a user fluid n: a substance (e.g. a liquid or gas) which tends to take the shape of a container front adj/n: distally disposed or a distally disposed site (e.g. a front of a syringe comprises the dispensing orifice)

gas n: a fluid which is neither solid nor liquid inferior adj: below in altitude (when used to denote relative position)

liquid n: a fluid which is neither solid nor gaseous, generally considered to be free flowing like water medial adj: occurring away from an outer edge; disposed near the center of (e.g. disposed away from an edge or periphery and in the vicinity of a center of gravity or axis of symmetry)

multi-chamber syringe n: a syringe having two disparate chambers which may contain different fluids in each chamber and from which the fluids are kept disparate through delivery from the syringe multi-chamber syringe-pre-flush configuration n: a complex syringe assembly comprising a multi-chamber syringe with a pre-flush tube attached $P_d$ n: pressure in a distal chamber plunger n: a portion of a syringe piston apparatus usually affixed to a syringe stem which is used to displace fluid within a syringe barrel pre-flush tube n: an extension for a syringe, usually a hollow, elongated tube affixed to a distal end of the syringe, the extension being filled with a flush fluid prior to delivery of contents from the syringe prime v: to fill liquid into a cavity generally by removing air therefrom (e.g. priming a gas separator)

$P_p$ n: pressure in a proximal chamber proximal adj: opposite of distal (e.g. a term which depicts placement nearer than a reference point)

rear adj: opposite from front (i.e. generally associated with a part of a syringe barrel which is proximal to a syringe user)

stem n: an elongated part which fits within a syringe barrel and is affixed to a plunger for the purpose of displacing fluid within the barrel stop n: a obstruction which is differentiated from friction or stiction, esp. an obstruction which halts displacement of a stopper or plunger superior adj: above in altitude (when used to denote relative position)

syringe n: a device used for injecting or withdrawing fluids upstream adj: a direction which is against the direction of flow from a syringe (opposite of downstream)

vial access device n: a device which generally has a cannula for piercing a membrane seal of a vial thereby providing external access to contents of the vial

BRIEF SUMMARY AND OBJECTS OF THE INVENTION

In brief summary, this novel invention alleviates all of the known problems related to dispensing hazardous medicines or other substances from a vial to a delivery syringe and therefrom to a site where each medicine is finally used. The instant invention disclosed herein employs a multi-chamber syringe which is disclosed in detail in Thorne, Jr. '304 and Thorne, Jr. '504 which are incorporated herein by reference.

In its currently preferred embodiment, the invention comprises a hermetically sealed valve assembly having a plurality of ports. Currently, the number of ports is four, although the number may vary by application and, in one configuration, only three ports are required.

As part of the valve assembly, a cannula subassembly with a make-before-break seal connection that provides seal contact before cannula piercing of a vial membrane which provides access via the cannula to medicine within the vial. To further reduce likelihood of substance exposure external to the vial and valve assembly, a filter may be affixed to the cannula, similar to the filter of the ChemoBloc® Vial Venting System, distributed by Kendall.LTP, of Tyco/Healthcare. As a practical matter, nearly all liquid transfer through the valve assembly may be accomplished by drawing liquid (applying pressures which are generally less than ambient air pressure) from one site to another through the valve as a considered preferred alternative to using positive pressure therefore. In all cases, any positive pressure resident in the valve assembly and attached parts is not greater than pressure required to displace a stem and associated plunger of a syringe which is in communication with the source of the resident pressure.

A key to providing an exposure protecting system is through use of a multi-chamber, sequential delivery syringe onto which is connected a pre-flush tube to form a multi-chamber-pre-flush syringe configuration. In the syringe filling mode, a distal end of the pre-flush tube is connected to a selected port of the valve assembly.

The multi-chamber syringe has a proximal chamber which is generally filled with a volume of flush and/or cleansing solution. Through the valve assembly, liquid from the vial is dispensed in various modes of operation into the distal chamber of the multi-chamber syringe through the flush tube. Once the medicine is so dispensed, a second volume of flush or cleansing solution is delivered into and through the flush tube to "rinse and clean" the port connecting site of the flush tube.

The pre-flush tube is subsequently occluded by crimping to retain the hazardous liquid proximal to the crimping site. After crimping the pre-flush tube, the pre-flush tube may be removed from the valve assembly (as last-entered flush liquid is resident at the connecting site) and capped with a protective cap for delivery to a site of use.

At the location of ultimate use, the protective cap may be removed and the associated pre-flush tube connected to a dispensing site. Note, that the integrity of the liquid flush interface is preserved by the cap and occluding crimp. Note also, that flush resident in the pre-flush tube is dispensed first, then the medicine is dispensed and, finally, flush from the proximal chamber of the multi-chamber syringe is dispensed. So performed, the finally dispensed flush acts to irrigate and so cleanse the connection where the pre-flush tube is connected to the dispensing site, thereby providing a site "rinsed and cleansed" of hazardous liquid for less dangerous handling.

In a first state, the valve assembly opens a communicating pathway between a syringe into which is drawn a measured amount of medicine. It is important to note that the valve may be used in a variety of modes. To clarify such variety, examples of use in two modes are provided as follows:

Mode 1

In a first mode, a small volume syringe is affixed to a second port (the vial being affixed to a first port) and used to draw in the measured amount of medicine from a vial while the valve assembly is disposed in a first state whereat a communicating pathway is opened between a cannula inserted into the vial and the port whereat the small volume syringe is connected. As is conventional practice, the small volume syringe is primed before the measured amount is drawn.

As the cannula and small volume syringe are affixed to the first and second ports, a multi-chamber-pre-flush syringe configuration is affixed to a third port and a flush syringe is affixed to a fourth port. In the first state, the multi-chamber-pre-flush syringe configuration is disposed to communicate with the flush syringe through the valve assembly. So connected, flush or diluent, which is preferably resident in the distal chamber of the multi-chamber syringe and pre-flush tube is drawn into the flush syringe and the multi-chamber syringe and pre-flush tube are thereby primed, with the distal chamber of the multi-chamber syringe emptied.

The valve assembly is then displaced to a second state whereat the second (small volume syringe) port is disposed to communicate with the third (multi-chamber-pre-flush syringe configuration) port. Contents of the small volume measuring syringe are drawn into the pre-flush tube and distal chamber of the multi-chamber syringe.

The valve assembly is returned to the first state whereat the fourth (flush syringe) port communicates with the third (multi-chamber-pre-flush syringe configuration) port. Sufficient flush or diluent is drawn from the flush syringe into the pre-flush tube to irrigate and rinse the connecting elements associated with the flush syringe and third port.

A crimping device is affixed to occlude the pre-flush tube. The pre-flush tube is disconnected from the third port and the third port is capped. The disconnected pre-flush tube is also capped and otherwise prepared for delivery to a site of use. After the third port is capped, used parts, other than the syringe configuration, should be delivered for appropriate disposal as hazardous waste.

Mode 2

In a second mode, a multi-chamber-pre-flush syringe configuration is affixed to the second port (a vial being affixed to the first port). The flush syringe is affixed to the third port. As a first step, the valve assembly is disposed in the second state whereat the flush syringe communicates with the multi-chamber-pre-flush syringe configuration through the valve assembly. So connected, flush, which is preferably initially resident in the distal chamber of the multi-chamber syringe and pre-flush tube is dispensed into the flush syringe and the multi-chamber syringe and pre-flush tube are thereby primed.

The valve assembly is then switched or displaced to the first state whereat the multi-chamber syringe is used to draw in a measured amount of medicine. As is conventional practice, the pathway between the vial and multi-chamber-pre-flush syringe configuration is primed and a predetermined, measured amount of medicine is drawn into the multi-chamber syringe and pre-flush tube. It should be noted that, due to size characteristics of the multi-chamber syringe, this mode 2 will not generally yield the precision of mode 1 which may use a syringe better sized and calibrated for small volume, accurate measurements.

The valve assembly is then returned to the second state whereat the second (multi-chamber-pre-flush syringe configuration) port is again disposed to communicate with the third (flush syringe) port. A sufficient amount of the contents of the flush syringe are drawn into the pre-flush tube and distal chamber of the multi-chamber syringe to rinse and cleanse connecting parts at the second port. A crimping device, such as a slide clamp, is affixed to occlude the pre-flush tube.

The pre-flush tube is disconnected from the second port and the second port is capped. The disconnected pre-flush tube is also capped and otherwise prepared for delivery to a site of use. As disclosed for used parts, supra, the valve assembly and associated, connected parts should be appropriately disposed of as hazardous waste.

Accordingly, it is a primary object to provide an apparatus which can be used to transfer hazardous liquid from a vial to a site of use without exposing contents of the vial exteriorly.

It is a critical object to provide, as a part of the apparatus, a transportable multi-chamber-pre-flush syringe configuration which receives and fully contains all of the liquid transferred from the vial and which provides a protective interface whereat the configuration may be connected to a final delivery site with safety.

It is a further primary object to provide distally and proximally disposed flush solutions which are maintained disparate from an internally enclosed volume of hazardous medicine, all disposed within a filled multi-chamber-pre-flush syringe such that no exposed interface is contaminated with the hazardous medicine.

It is a principle object to provide a hermetically sealed valve assembly having a plurality of sealable connecting ports and structure which is switchable to two stable states, whereby at lease one communicating pathway is provided in each state between a predetermined pair of the ports.

It is an important object to provide a hermetically sealed hazardous material transfer system wherethough fluids are transferred at pressures less than surrounding ambient pressure to reduce likelihood of inadvertent release of hazardous to the ambient environment.

These and other objects and features of the present invention will be apparent from the detailed description taken with reference to accompanying drawings.

BRIEF DESCRIPTION OF THE DRAWINGS

FIG. 5 is perspective of an outer housing of the valve assembly seen in FIG. 1.

FIG. 6 is a side elevation of a cylindrical which is displaced into the housing seen in FIG. 5 for use, the rod having a plurality of internally disposed pathways.

FIG. 7 is a side elevation of the cylindrical rod seen in FIG. 6, but rotated ninety degrees.

FIG. 8 is a side elevation of the movable cylindrical rod seen in FIG. 7, but rotated ninety degrees.

FIG. 9 is a view of the one end of the cylindrical rod seen in FIGS. 6-8.

FIG. 9A is an O-ring used in association with the movable cylindrical rod seen in FIGS. 6-8.

FIG. 10 is a perspective of one of the knobs which is affixed to an end of the cylindrical rod to facilitate rotating and displacing the cylindrical rod.

DETAILED DESCRIPTION OF THE ILLUSTRATED EMBODIMENTS

In this description, when the term proximal is used relative to a part or the segment of a device, it is a part which is in closer proximity to a user of the device. The term distal refers to a part or segment generally away from the user. Reference is now made to the embodiments illustrated in FIGS. 1-23 wherein like numerals are used to designate like parts throughout.

Figure 1:
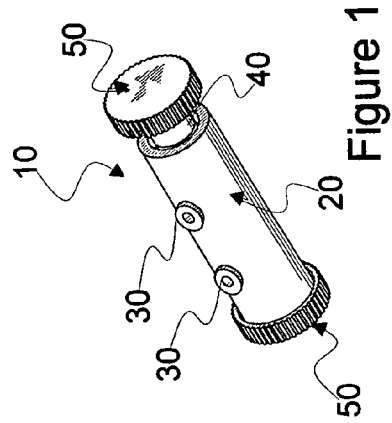
FIG. 1 is a perspective of valve assembly according to the present invention.

A valve assembly 10 is seen in FIG. 1. Valve assembly 10 comprises an outer, hollow, cylindrical housing 20 which has a plurality of externally accessible connecting ports, generally numbered 30. Disposed within the hollow of the housing is a close fitting cylindrical rod 40. Disposed on each end of cylindrical rod 40 is a handle, generally numbered 50, by which rod 40 is captured, rotated and displaced within housing 20.

Figure 2:
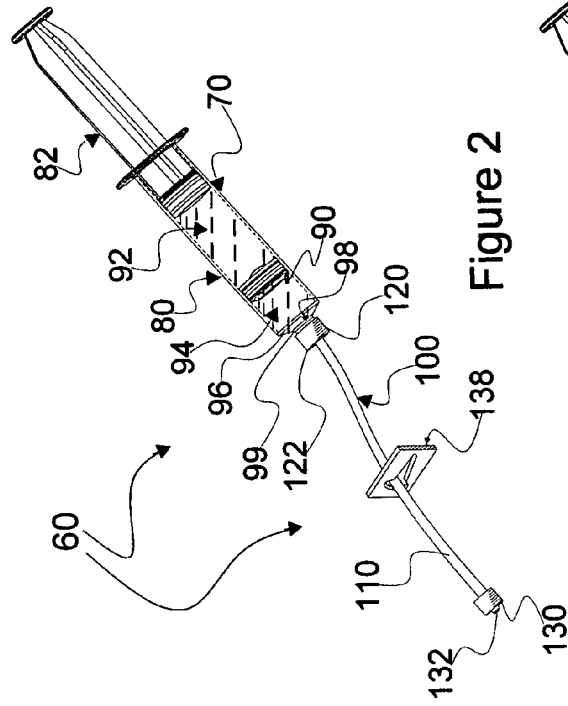
FIG. 2 is a perspective of a multi-chamber-pre-flush syringe which is a key part used with the valve assembly in transferring hazardous fluids from a vial to the syringe for medical use.

A multi-chamber-pre-flush syringe configuration 60 is seen in FIG. 2. A key part of configuration 60 is a multi-chamber syringe 70. Details of design and operational modes of a multi-chamber syringe, of which syringe 70 is an example, may be found in Thorne, Jr. '304 and Thorne, Jr. '504, which are incorporated herein by reference.

Syringe 70 generally has an elongated hollow barrel 80 in which a stem and rear plunger configuration 82 is moved to displace fluids. In addition, syringe 70 has a valved stopper 90 distally disposed relative to configuration 82 whereby barrel 80 is divided into two disparate proximal and distal chambers, numbered 92 and 94, respectively. At a distal end 96, barrel 80 is closed about an orifice 98 and preferably a luer fitting 99, affixed thereto.

Affixed to fitting 99 is a tube set 100. Set 100 includes an elongated tube 110, a syringe fitting connector 120 on a proximal end 122 and another luer fitting 130 at a distal end 132. Disposed between ends 122 and 132 is a slide clamp 138 which is used to selectively occlude tube 110, as disclosed in detail hereafter. It should be noted that fluids may be displaced through tube 110 in and out of chamber 94 in a manner similar to displacement of a conventional syringe so affixed to tube set 100.

Figure 3:
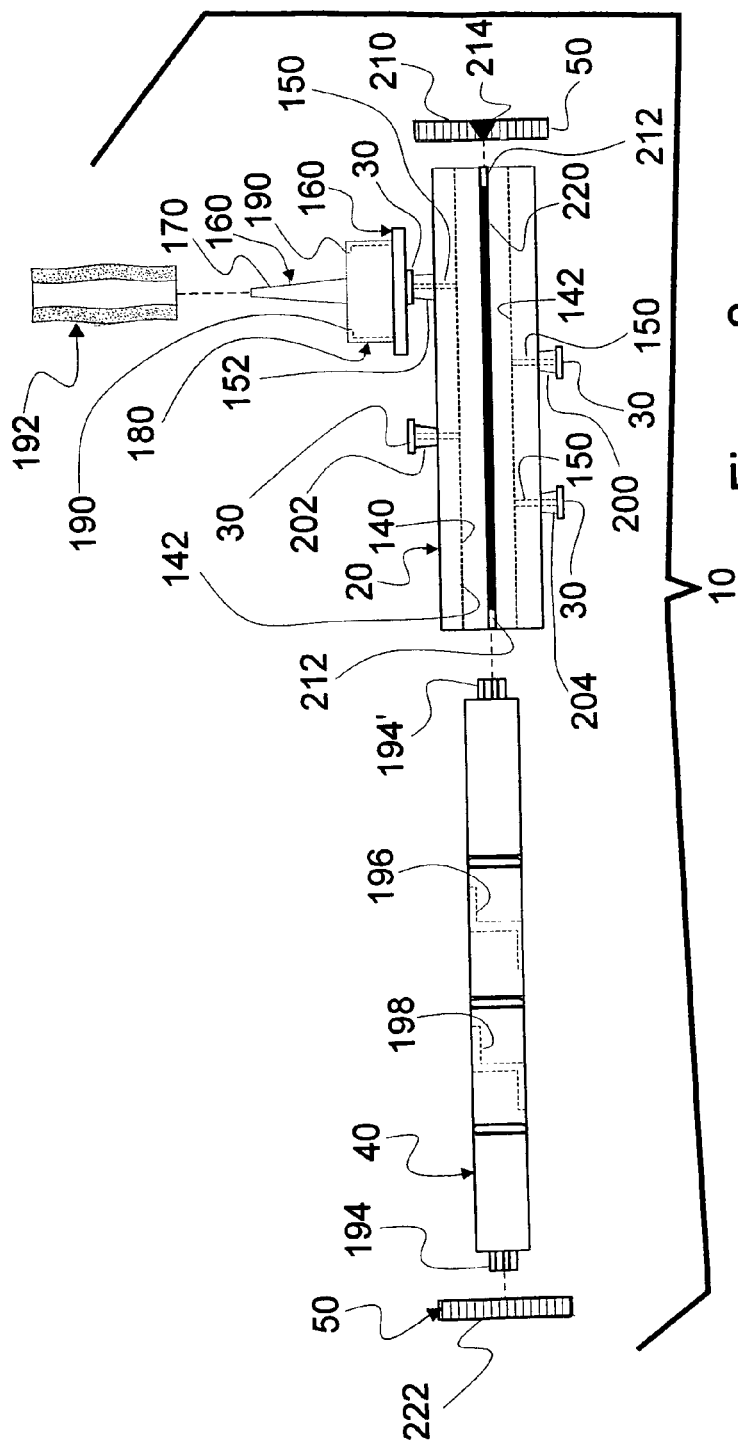
FIG. 3 is an exploded view of a side elevation of parts of the valve assembly of FIG. 1.

An exploded view of valve assembly 10 is seen in FIG. 3. Housing 20, having a hollow internal cylinder 140 outlined by hidden lines, generally numbered 142. Cylinder 140 has a plurality of and communicating through holes, generally numbered 150, to provide access to ports 30.

One of the ports 152 is a female lure fitting which is securely affixed to a ChemoBloc Vial Venting System, referenced as system 160. As disclosed supra, system 160 has a filter associated with a vial access which inhibits dispensing caustic contents from a vial to an ambient environment while permitting air to filter into the vial when a pressure which is negative relative to ambient pressure resides in the vial. In this manner, liquid may be drawn from a vial while being replaced by ambient air. While other vial access systems with membrane piercing cannulas may be used within the scope of the present invention, system 160 is particularly useful in permitting access to and transferring fluids at pressures which are generally less than ambient atmospheric pressure.

As is well known and in commercial use, system 160 has a membrane piercing cannula 170 which contains a first fluid or medicine communicating pathway and a second fluid communicating pathway for air being introduced into an attached vial. As a vial, not shown in FIG. 3, should be securely affixed about cannula 170 and to housing 20, affixed to system 160 is a vial connector 180. Vial connector 180 has a plurality of internally directed leaves 190 which are displaceable upon insertion of a vial cap into connector 180, but which provide a secure attachment, impeding release of the vial cap after insertion. Such connectors with leaves are well known in paint can lid attachments.

As seen in FIG. 3, a compressible hollow cylindrical seal 192 is disposed to be displaced about cannula 170 to provide a guard against fluid being released from a vial when pierced by cannula 170. Seal 192 is shaped to fit closely about cannula 170 yet provide a contact with a connecting vial before cannula 170 pierces the vial access membrane. Such seal 192 make-up, shape and function is addressed in detail hereafter.

Cylindrical rod 40 is sized and shaped to snugly, but displaceably fit, to be laterally and rotationally displaced within hollow internal cylinder 140 while providing liquid containment therebetween. On each end of rod 40, end connecting elements, numbered 194 and 194', provide means for connecting to each knob 50.

Note that, rod 40 has a plurality of continuous, internally disposed connecting pathways, shown by hidden lines and numbered 196 and 198. In the angular orientation of rod 40 as seen in FIG. 3, rod 40 may be inserted into housing 20 and displaced such that pathway 196 communicates with port 152 to provide a continuous pathway to a port 200. Concurrently, a continuous pathway from a port 202 to a port 204 is likewise provided. Further, when rod 40 is so oriented and displaced, and a knob 50, affixed to end connecting element 194' (so affixed, knob 50 is designated by the number 210), is disposed to interface with an interlocking slot 212'. Such displacement is easily determined by correspondence of visible indicia, such as indicia 214 on knob 210 and indicia 220 on housing 20 (see FIG. 3).

Figure 4:
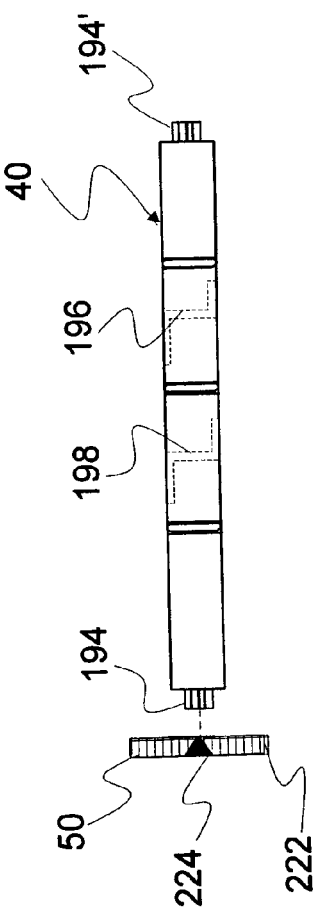
FIG. 4 is an exploded view of a side elevation of a portion of the parts seen in FIG. 3, the parts in FIG. 4 being rotated relative to the same parts seen in FIG. 3.

Reference is now made to FIG. 4 wherein rod 40 is rotated 180 degrees, about the long axis thereof, relative to disposition of rod 40, as seen in FIG. 3. Notice orientation of pathways 196 and 198. Usefulness of such a change in orientation is disclosed fully hereafter. Also note that knob 50 (having a reference of knob 222) associated with end 194 is also rotated to display indicia 224 which is in line with indicia 220 (see FIG. 3) when valve assembly 10 is fully assembled.

Housing 20 is seen apart in FIG. 5. In FIG. 5, ports 200 and 204 are hidden, but are female luer connections similar to port 202. Port 152 has a male luer fitting. Slots 212 and 212' are triangular in shape in FIG. 5 demonstrating that geometric shapes of such slots may be varied. Such shapes may include self latching geometries which conform with latches of an associated knob 50 to releasibly interlock to provide a stable state while liquid transfer occurs.

Attention is now directed to FIGS. 6-9 wherein rod 40 is seen in various states of rotation. In FIG. 6, pathway 196 is seen to comprise a lateral opening slot 226 and an associated through-hole 228. Similarly, pathway 198 comprises a lateral opening slot 230 and a through-hole 232. In FIG. 7, wherein rod 40 is rotated 90 degrees counterclockwise relative to rod 40 in FIG. 6, pathways 196 and 198 are outlined by hidden lines 196' and 198', respectively. A further counterclockwise rotation of rod 40 is seen in FIG. 8, wherein pathway 196 is seen to comprise an additional slot 226' which communicates with hole 228. Pathway 198 likewise comprises a slot 230' which communicates with hole 232. Rod 40 is preferably sized and shaped such that wall 140' of hollow internal cylinder 140 provides a liquid-sealing enclosure about each slot.

As such, housing 20 and rod 40 are each preferably made by injection molding using a self lubricating synthetic resinous material. Such a material may be medical grade polypropylene, or other materials which are substantially biologically inert, moldable, stable and self-lubricating. Knob 50 may be likewise molded from similar materials.

As it is important that valve assembly 10 be hermetically sealed, a mere close fit of rod 40 into hollow cylinder 140 is not considered sufficient to assure a sufficiently protective seal. Therefore, a plurality of circular grooves, generally numbered 240 are also molded or otherwise contoured into rod 40 such that o-rings may be employed to further affect a more sure seal both against release of material to ambient surroundings and between pathways. Such o-rings are not shown in FIGS. 6-8, but such use of o-rings is well known in medical and seal arts. An example of such an o-ring, numbered 240' is seen in FIG. 9A.

A knob 50 which may be used as knob 210 and as knob 224 is seen in FIG. 10. Knob 50 is preferably a circular, disk-shaped part having grippable knurled edges 242. Medial to edges 242 is a depressed section 244 which surrounds a hub 246. Hub 246 has a centrally disposed hole section 248 which is sized and shaped to conformably be affixable to each end 194 and 194' of rod 40. Further, section 248 comprises a key slot 250 which is disposed to align with a key 250' disposed upon an associated rod 40 end (either 194 or 194') by which knob 50 is affixed to rod 40 to assure correct alignment relative to indicia 214 and 224 and to indicia 220 and, therefor, to pathways 196 and 198. Note, in FIG. 9 that end 194' has a key 250' which aligns with key slot 250 to assure such proper orientation of knob 50 relative to housing 20 and rod 40. Also, knob 50 has a raised structure 252 which is sized and shaped to insertably catch within associated slot 212 or 212' to define a permissible fluid transfer disposition of valve assembly 10.

Figure 11:
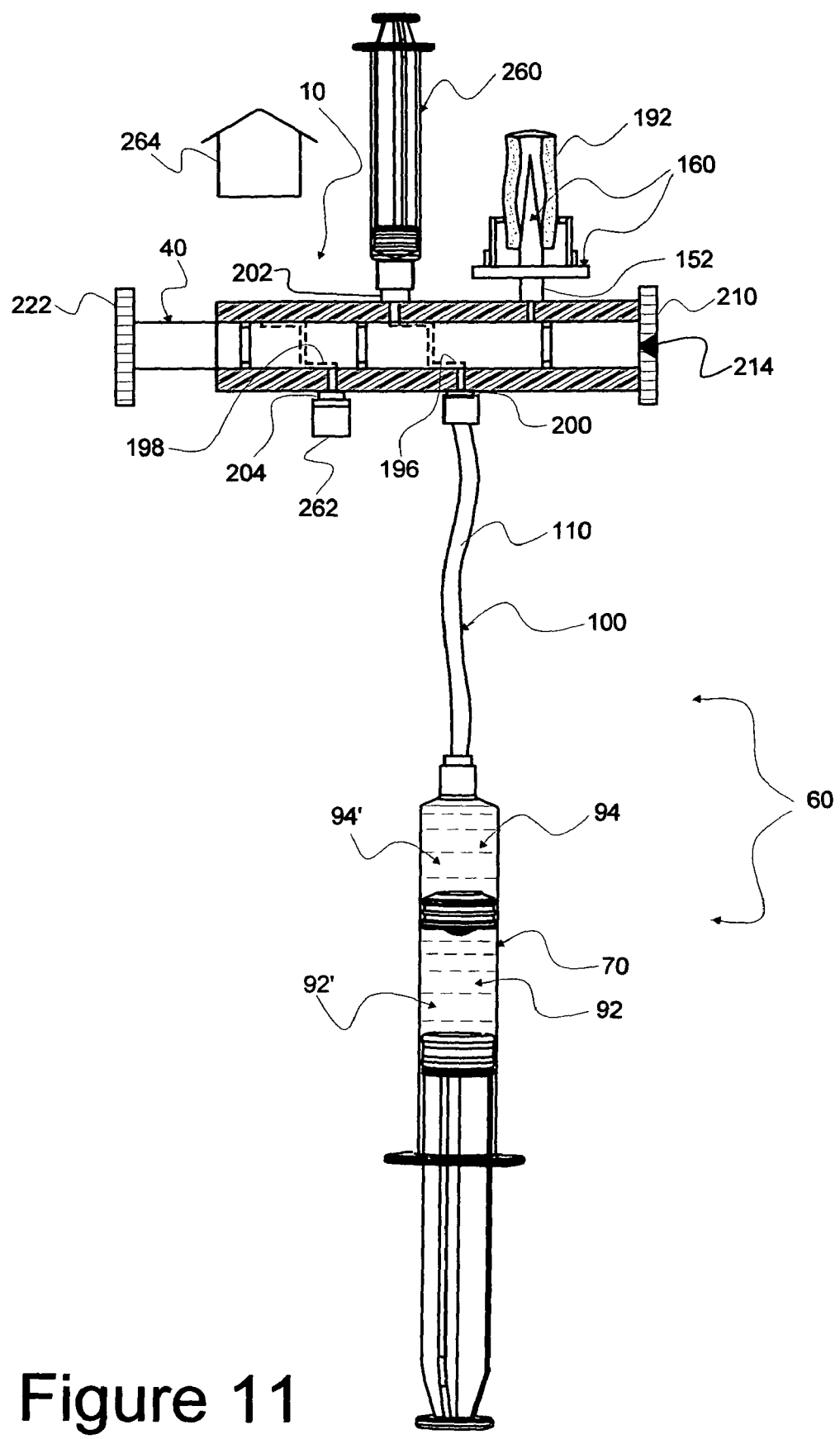
FIG. 11 is a schematic diagram of a first step of an exemplary method according to the present invention for transferring fluid from a vial into a syringe for use in a medical procedure.

While valve assembly 10 may be used in diverse ways to transfer liquids with safety, the following two examples exemplify methods of use. Reference is first made to FIGS. 11-15 where a multi-chamber syringe 70 is used to directly access liquid from a vial in an initial example. Initial status of valve assembly 10 is seen in FIG. 11, with indicia 214 visible and in alignment with indicia 220 (indicia 220 is not seen in FIG. 11, but may be seen in FIGS. 3 and 5).

Note, a vial venting system 160 is affixed to port 152. System 160 is preferably securely affixed thereat so that removal is either impossible or extremely difficult. A multi-chamber-pre-flush syringe configuration 60 is firmly, but releasibly affixed in fluid-tight connection to port 200. Though not necessary within the scope of the present invention, multi-chamber syringe 70 contains a flush solution 94' in distal chamber 94 and a flush solution 92' in proximal chamber 92. As such, syringe 70 may be the only pre-filled syringe required to operate valve assembly 10.

A conventional syringe 260 is provided as an empty syringe and affixed to port 202. Port 204 is capped with a sealing cap 262.

Also note that rod 40 is rotated and displaced such that pathway 196 interconnects ports 200 and 202. As a first step flush liquid 94' is drawn from chamber 94 into syringe 260 through pathway 196, by displacement action in direction of arrow 264. As shall commonly be the case, it is recommended that most, if not all, displacement of liquid via valve assembly 10 be performed by drawing liquid from one vessel to another to maintain a negative pressure relative to the surrounding ambient pressure and thereby further reduce likelihood of any matter escaping from valve assembly 10 during fluid transfer.

Figure 12:
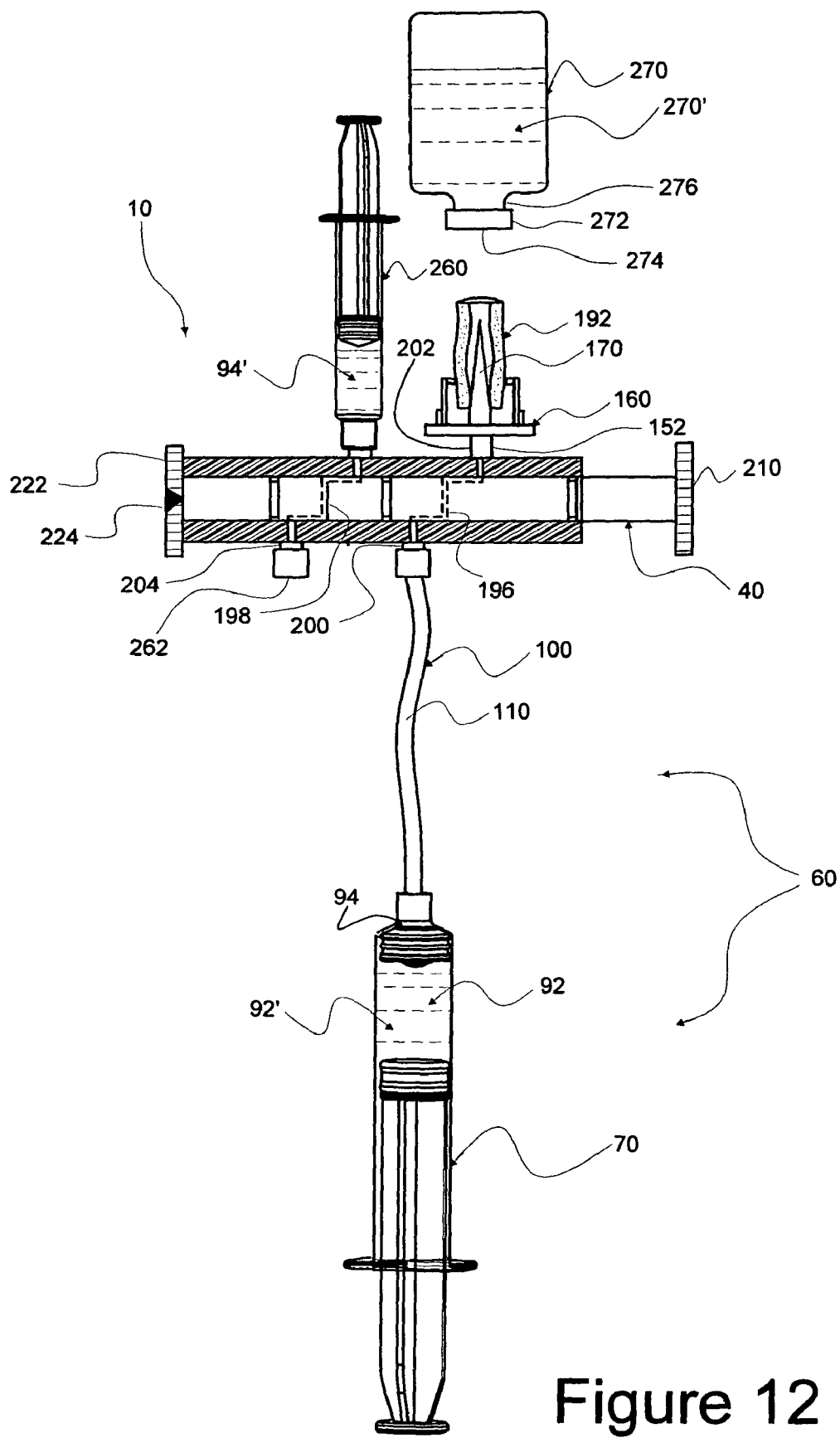
FIG. 12 is a schematic diagram of a second step following the step characterized in FIG. 11.

Reference is now made to FIG. 12 wherein a selected vial 270 contains a volume of transferrable medicine 270'. Vial 270 is generally closed and sealed by a metal ring 272 which surrounds a pierceable membrane 274 (not shown, but well known in vial use arts). Ring 272, affixed to vial 270, provides a circular groove 276 between ring 272 and vial 270 which may be used to securely affix an attachment to secure vial 270 to a connecting fixture. Note, in FIG. 12, that transfer of liquid 94' from chamber 94 into syringe 260 is accomplished.

Figure 13:
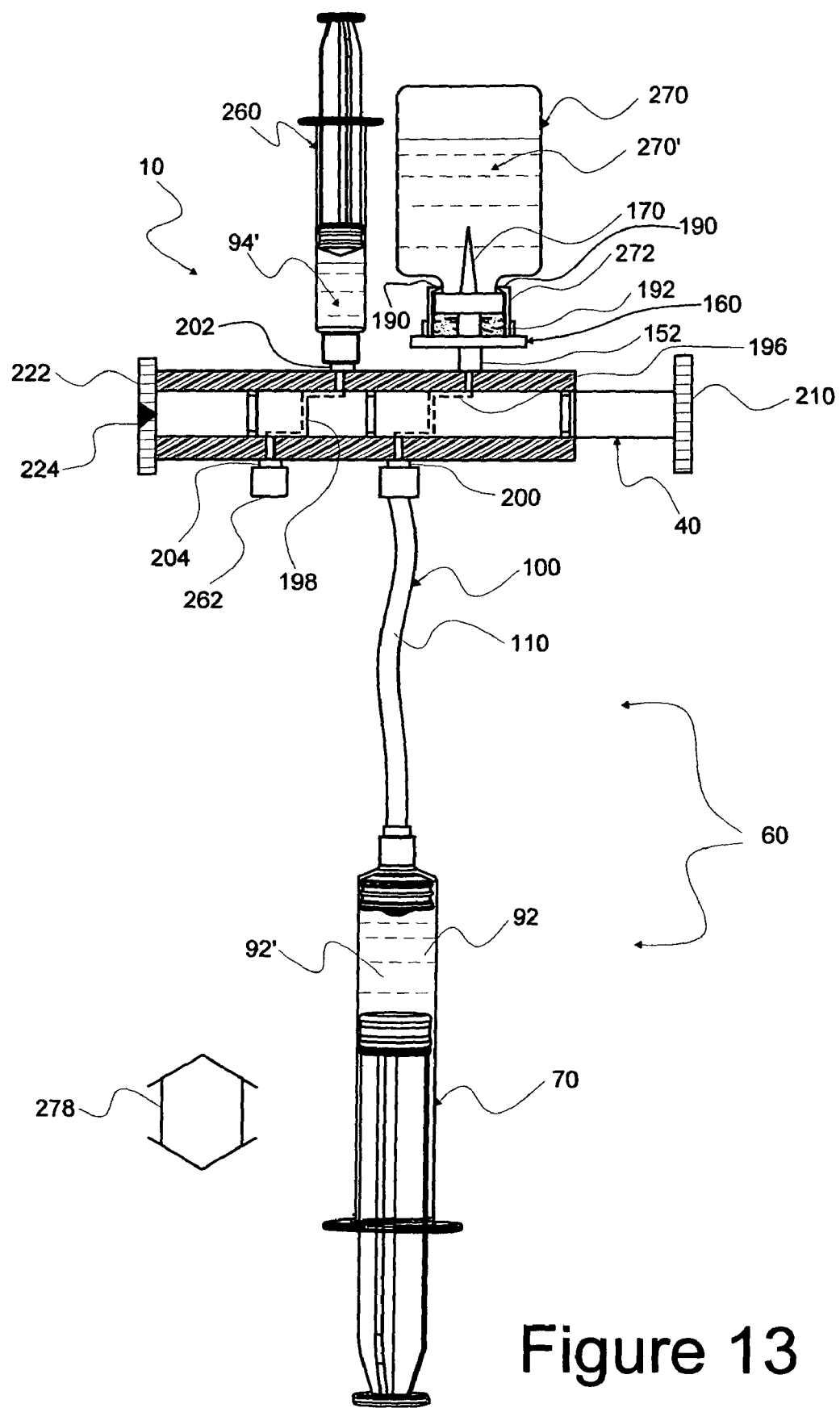
FIG. 13 is a schematic diagram of a third step following the step characterized in FIG. 12.

As seen in FIG. 13, vial 270 is displaced to pierce membrane 274 (see FIG. 12) and securely affix ring 272 (and vial 270) to connector 180 (see also FIG. 3), with medially directed leaves 190 firmly resisting release of ring 272 from system 160. Note that such installation of vial 270 about cannula 170 compresses and compacts seal 192 about cannula 170 to further deter matter from exiting valve assembly 10 during cannulation and liquid transfer. A seal such as seal 192 may be made of flaccid synthetic resinous material, such as latex free rubber or closed cell foam.

Once vial 270 is disposed as seen in FIG. 13, medicine 270' may be drawn from vial 270 into syringe 70 and tube set 100 of multi-chamber-pre-flush syringe configuration 60. As is well known in syringe handling art, any gas resident in cannula 170, pathway 196 and configuration 60 should be purged as part of the drawing of liquid from vial 270 which may require limited bidirectional displacement of a stem of syringe 70 as indicated by arrow 278. It should be noted that liquid 270' volume drawn from vial 270 is replaced by air passing through a filter associated with system 160.

Figure 14:
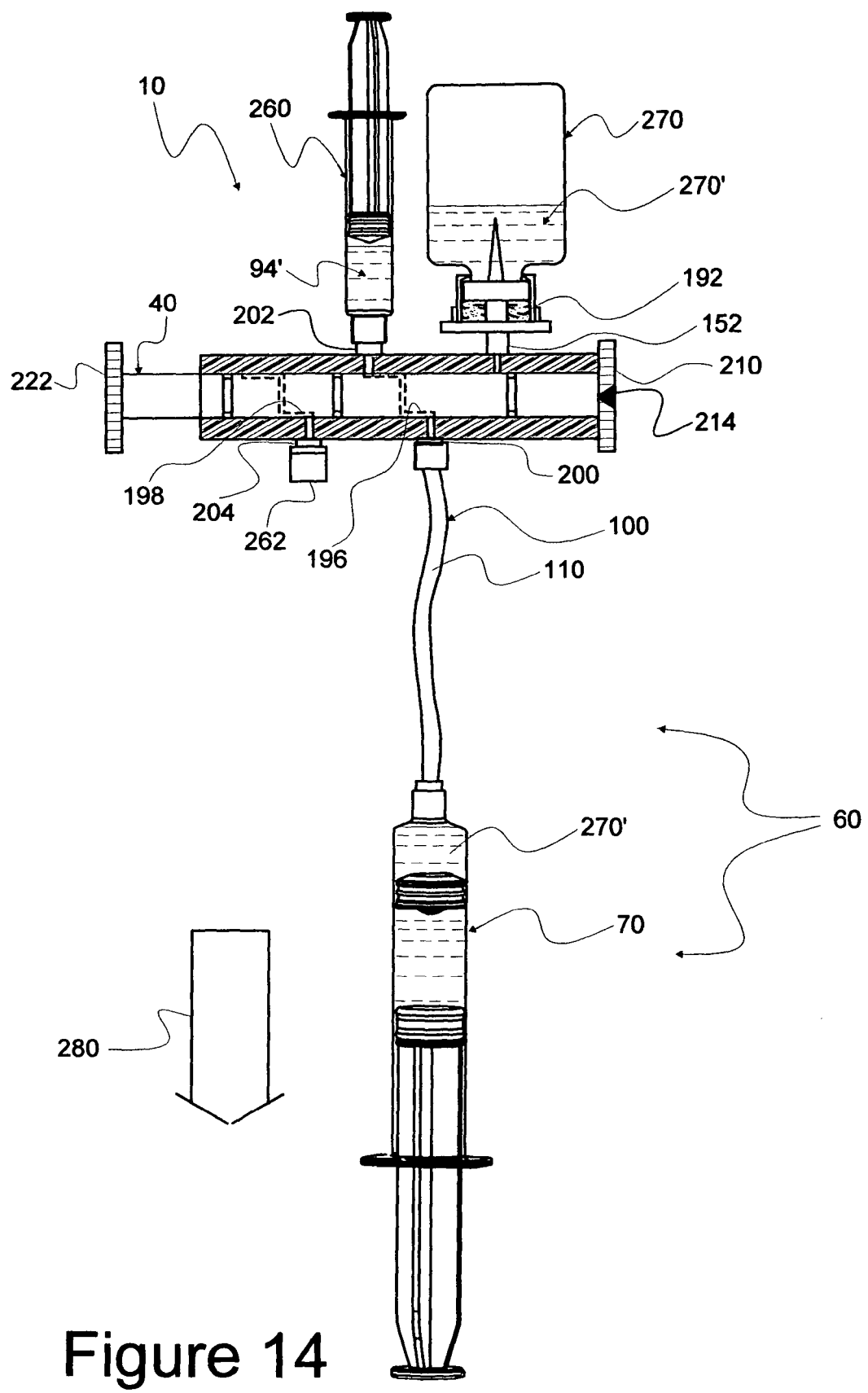
FIG. 14 is a schematic diagram of a fourth step following the step characterized in FIG. 13.

Once a desired volume of medicine is drawn into configuration 60, rod 40 is rotated and displaced to permit communication between ports 200 and 202 as seen in FIG. 14. Sufficient flush is drawn (in direction of arrow 280) to cleanse port 200 and fill tube set 100 with flush. A clamping element such as slide clamp 138 (see FIG. 15) is displaced to occlude tube 110 of tube set 100 preparatory to removing configuration 60 from valve assembly 10.

Figure 17:
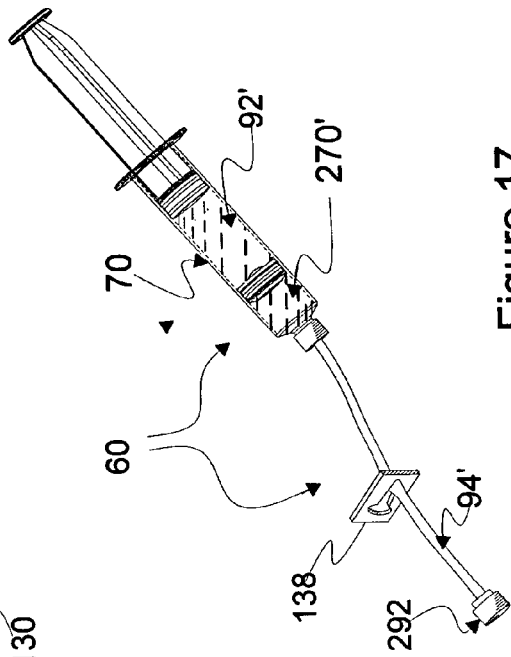
FIG. 17 is a perspective of a multi-chamber-pre-flush syringe configuration with an end of the pre-flush tube capped.
Figure 16:
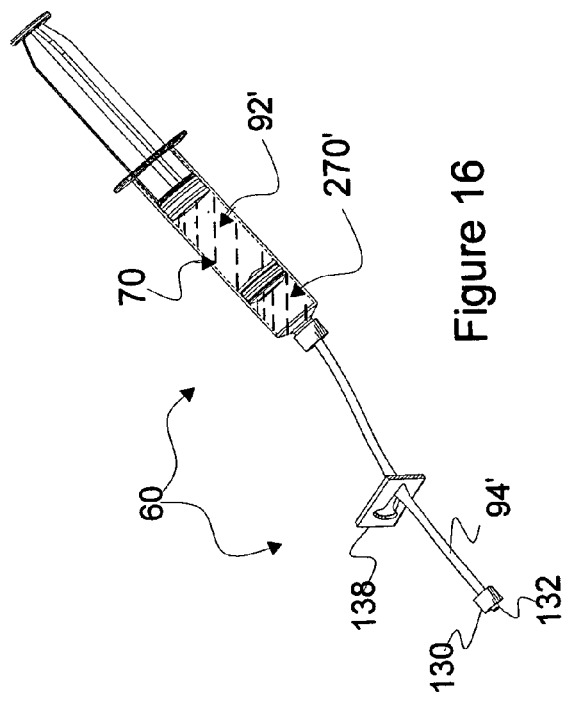
FIG. 16 is a perspective of a multi-chamber-pre-flush syringe configuration with a pre-flush tube clamped and removed from the valve assembly.
Figure 15:
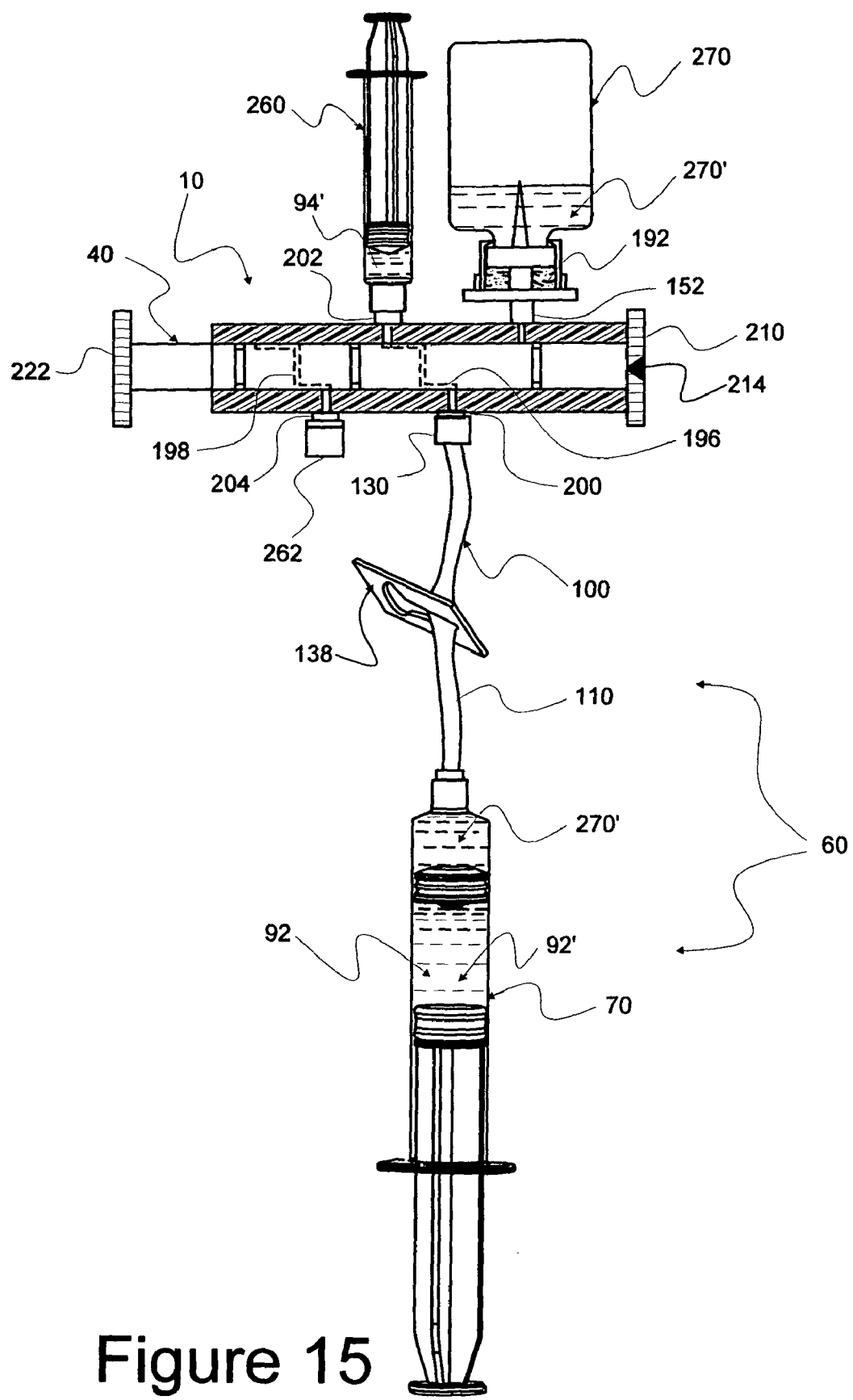
FIG. 15 is a schematic diagram of a step following the step characterized in FIG. 14 wherein a pre-flush tube of a multi-chamber-pre-flush syringe configuration is clamped and occluded preparatory to removing the configuration from the valve assembly.
Figure 18:
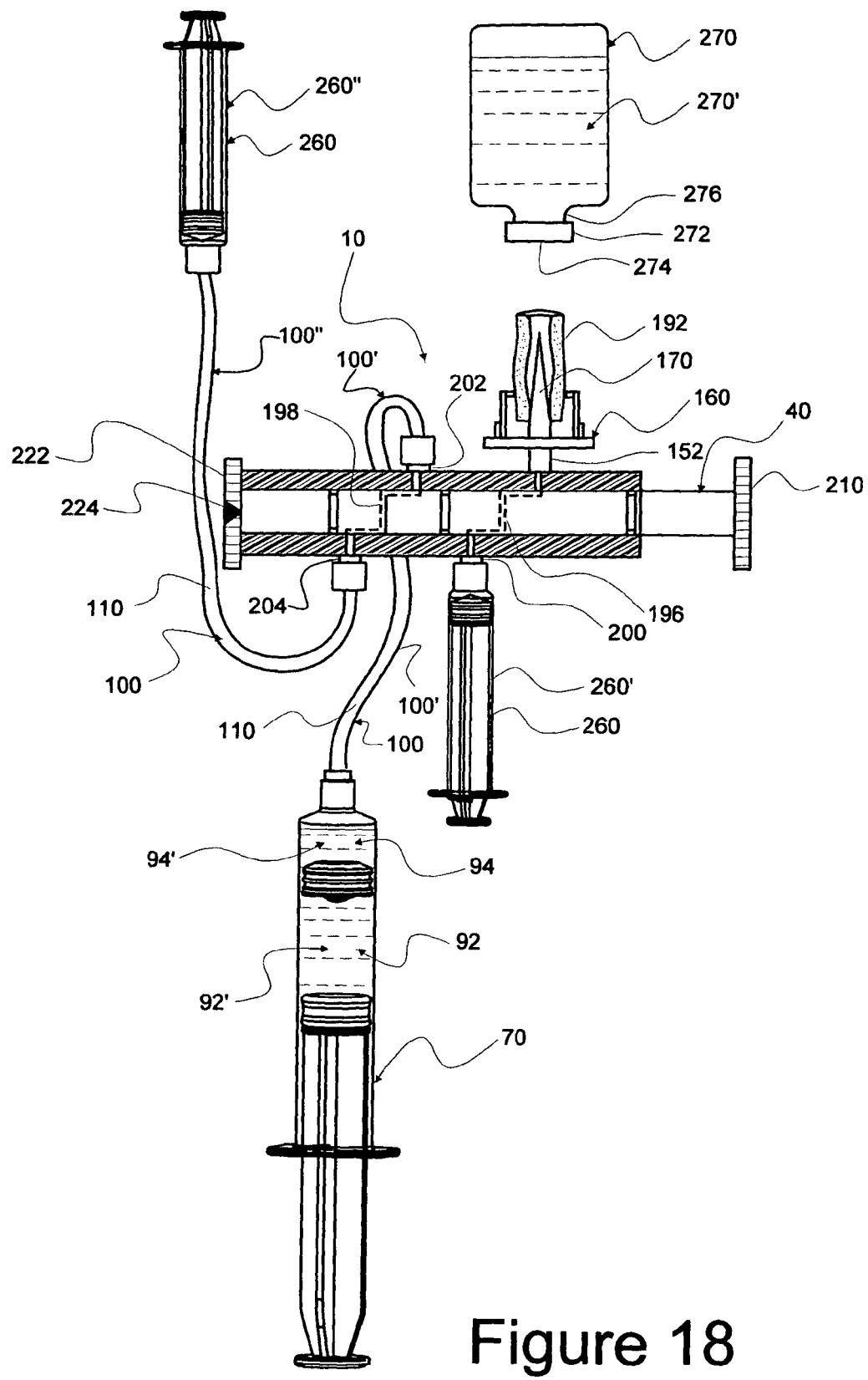
FIG. 18 is a schematic diagram of a first step of another exemplary method according to the present invention for transferring fluid from a vial into a syringe for use in a medical procedure.

As seen in FIG. 16, luer fitting 130 may now be disconnected from port 200 (see FIG. 15). Danger related to liquid resident at tube set 100 end 132 is minimized as a result of flush liquid 94' having replaced medicine 270' thereat. As seen in FIG. 17, end 132 is preferably capped with a cap 292, which is similar in form and function to cap 262 for closure and sterility purposes.

At a site of use (not shown), cap 292 is removed, pre-flush 94' is first dispensed from tube 110, followed by dispensing of the dose of measured medicine 270' contained in chamber 94 of syringe 70. Then, as fully disclosed in Thorne 504 and other U.S. Patent Applications from which this Patent Application continues-in-part, flush solution 92' is sequentially dispensed to again cleanse end 132 (see FIG. 16) and connecting attachments used in delivery of medicine 270' to alleviate hazards associated with matter associated with medicine 270' to medical technicians, cleaning personnel and others who might come in contact with a used configuration 60 or sites into which medicine 270' is dispensed. In similar fashion, a cap should be placed upon port 200, from which configuration 60 has been removed, and valve assembly 10 rod 40 should be retained in the state seen in FIG. 15 to assure residual portions of medicine 270' are fully retained within valve assembly 10 throughout appropriate disposal procedures.

Selected steps in a second example are seen in FIGS. 18-23 (and in FIGS. 16 and 17, as removal of a configuration 60 is similar to removal of a configuration 60 from valve assembly 10 in the initial example. A selected vial 270, ready for attachment to system 160 is seen separate from valve assembly 10. System 160 is securely affixed to valve assembly 10 at port 152. A first conventional syringe 260, referenced by 260' and being sized and shaped to provide a predetermined accuracy of a desired measured dose of medicine 270' to be drawn to be from vial 270 is affixed to port 200. A multi-chamber-pre-flush syringe configuration 60, having a first tube set 100, which is referenced as tube set 100', is affixed to port 202 with syringe 70 being inferiorly disposed relative to port 202. It should be noted that such a disposition of syringe 70 relative to port 202 is preferred to simplify priming of chamber 94 and tube 110 of associated tube set 100'. A second conventional syringe 260, referenced as syringe 260", is affixed to a second tube set 110, referenced as tube set 100", and therethrough affixed to port 204. Second conventional syringe 260' is disposed superior to port 202 to facilitate priming of chamber 94 and first tube set 100'.

Figure 19:
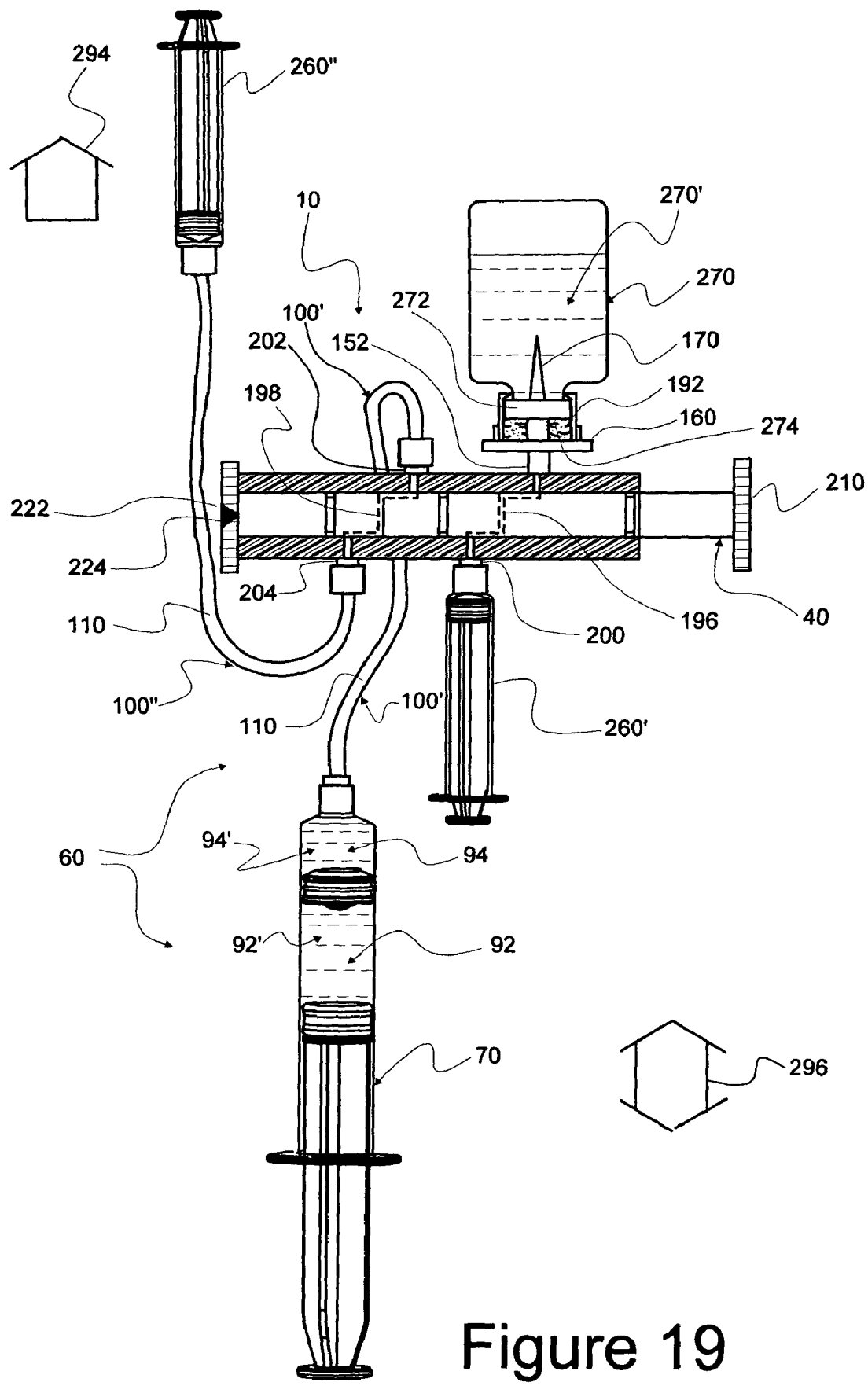
FIG. 19 is a schematic diagram of a second step following the step characterized in FIG. 18.

Note that rod 40 is disposed such that pathway 198 interconnects port 202 with port 204 and pathway 196 interconnects port 200 with port 152. As seen in FIG. 19, selected vial 270 is disposed to communicate medicine contents 270' trough cannula 170 to port 152, seal 192 having been compressed about cannula 170 and membrane 274 to assure against loss of matter from vial 270 into the surrounding environment.

Figure 20:
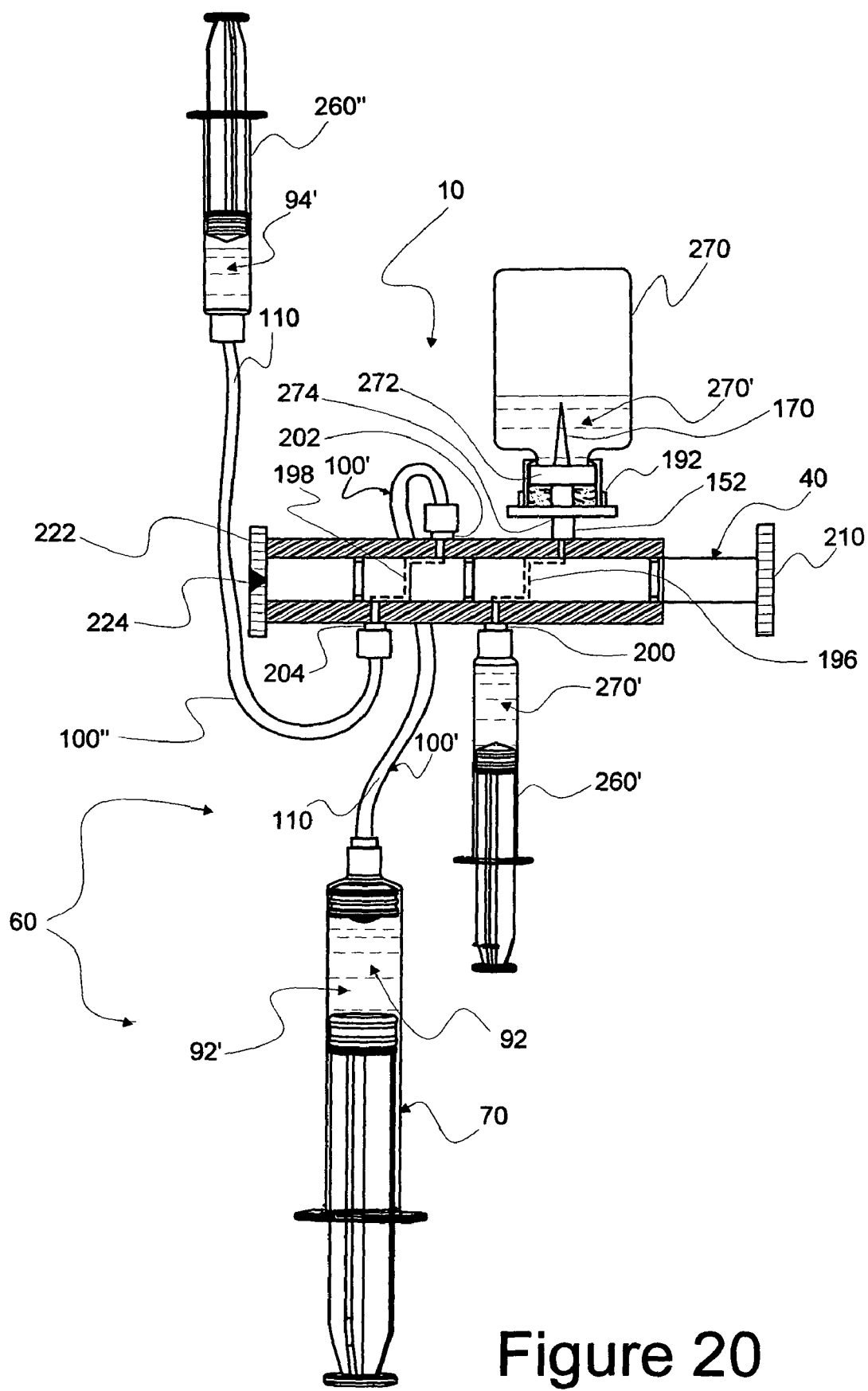
FIG. 20 is a schematic diagram of a third step following the step characterized in FIG. 19.

With rod 40 remaining as seen in FIG. 19, flush contents 94' of chamber 94 of syringe 70 is drawn into syringe 260" as indicated by arrow 294. As indicated supra, it is preferable to draw liquid from one container to another to maintain pressure within each syringe and assembly 10 negative relative to ambient pressure and thereby reduce likelihood of matter escaping during fluid transfer. Also, a measured, predetermined volume of medicine 270' is drawn into syringe 260' from vial 270 via pathway 196. Note direction of arrow 296, indicating drawing of fluid into syringe 260', with only a moderate amount of positive pressure being required to be applied to prime syringe 260' and pathway 196 due to the small volume of gas in evacuated syringe 260' and pathway 196. It should be emphasized that syringes 260' and 260" should initially be in an evacuated state to minimize gas content prior to use. In FIG. 20, a completed state of fluid transfer into syringes 260' and 260" is seen.

Figure 21:
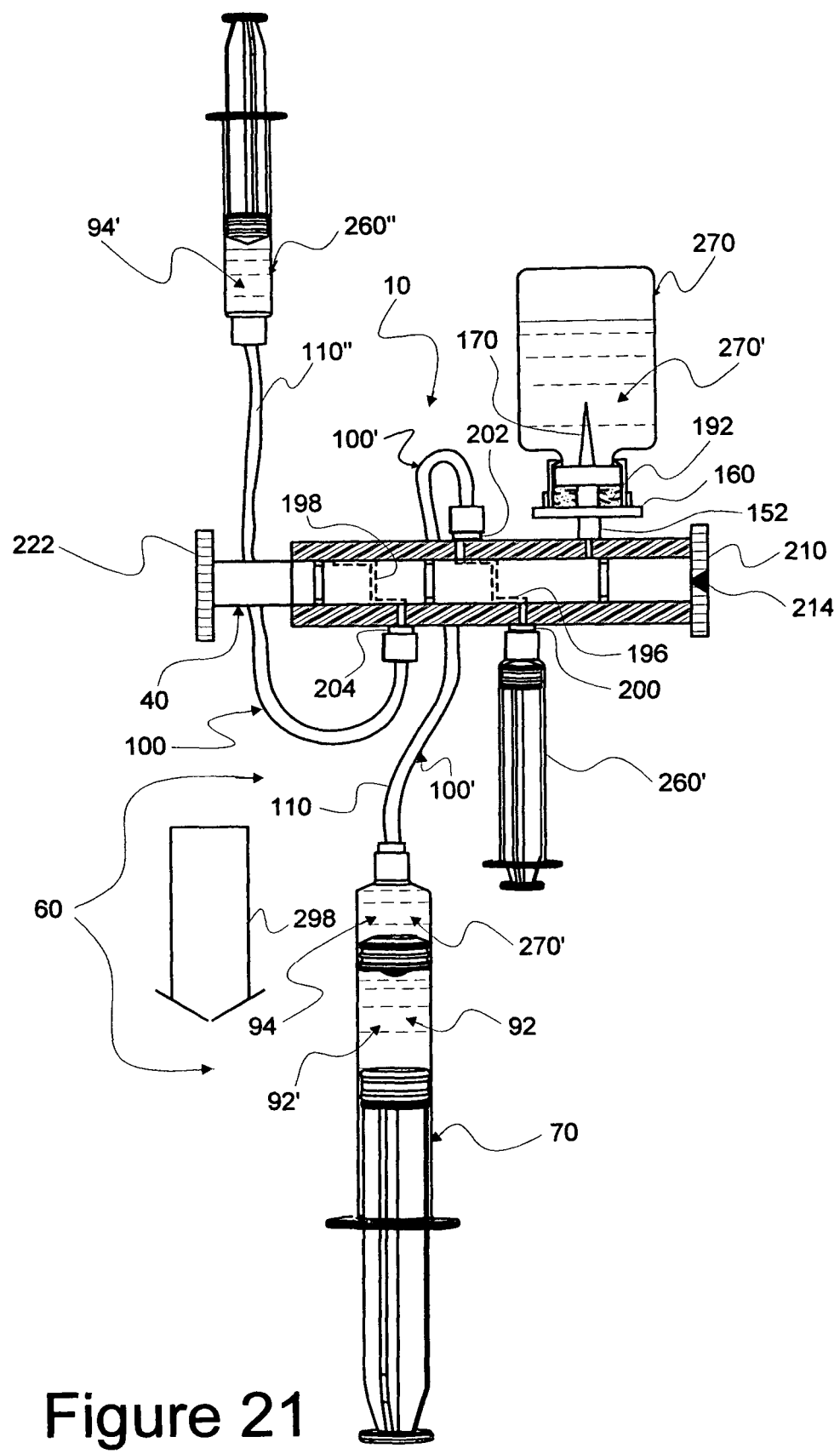
FIG. 21 is a schematic diagram of a fourth step following the step characterized in FIG. 20.

In FIG. 21, rod 40 is rotated and displaced such that pathway 196 interconnects ports 200 and 202. When so disposed, as indicated by arrow 298, the measured portion of medicine 270' is drawn from syringe 260' into tube set 100 and chamber 94 of syringe 70. It may also be noted that the volume of medicine 270' resident in pathway 196 does not change during fluid transfer and, therefore, does not affect accuracy of the volume measured in syringe 260'.

Figure 22:
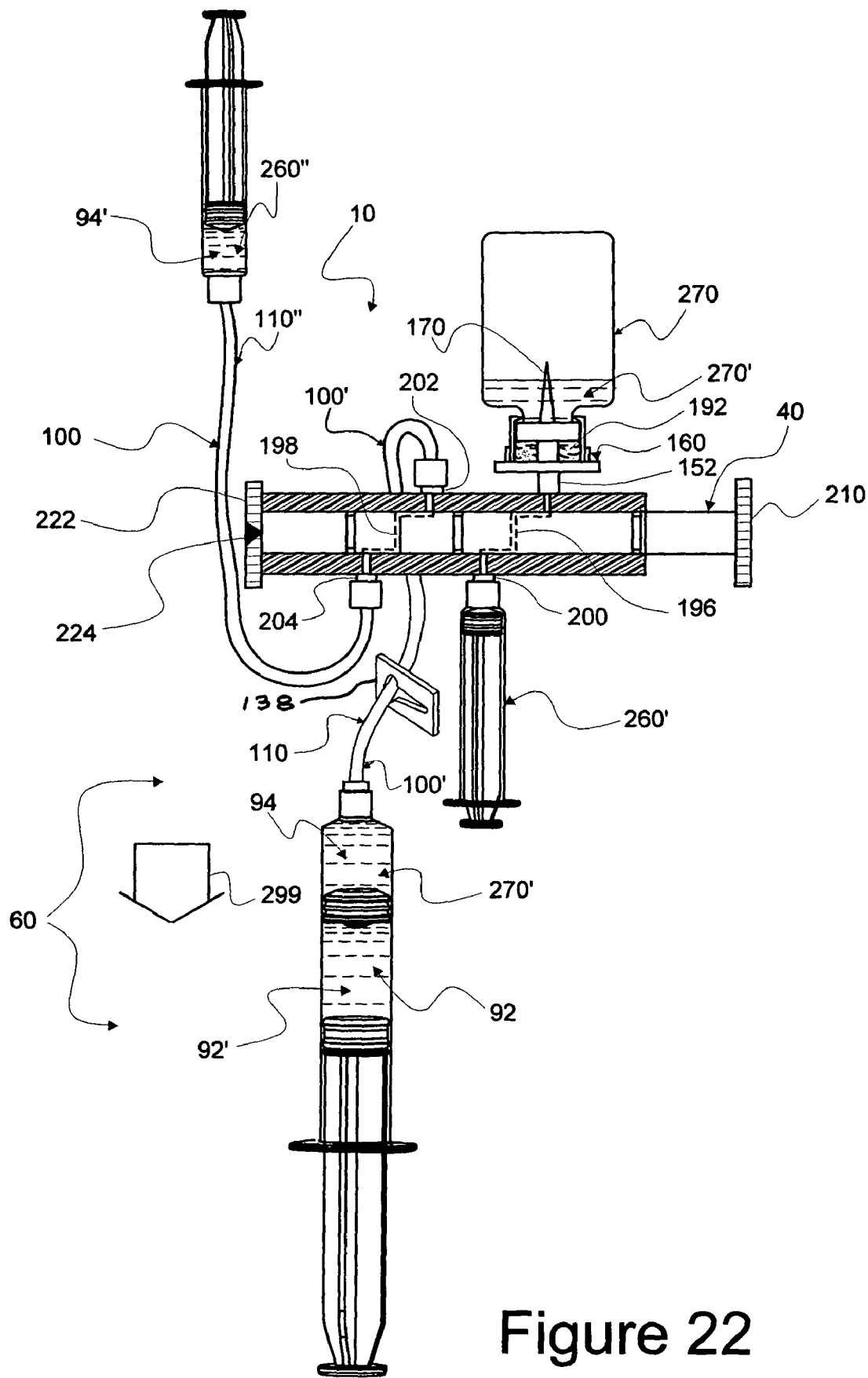
FIG. 22 is a schematic diagram of a fifth step following the step characterized in FIG. 21.

As a final fluid transfer step, rod 40 is again rotated and displaced to interconnect ports 202 and 204 via pathway 198, as seen in FIG. 22. As indicated by arrow 299, flush liquid 94' is drawn from syringe 260" to flush through port 202 and preferably a major portion of tube 110 of tube set 100', thereby flushing and washing to clear pathway 196 and connecting parts at port 202 of medicine 270', leaving a residue of flush liquid 94' thereat.

Figure 23:
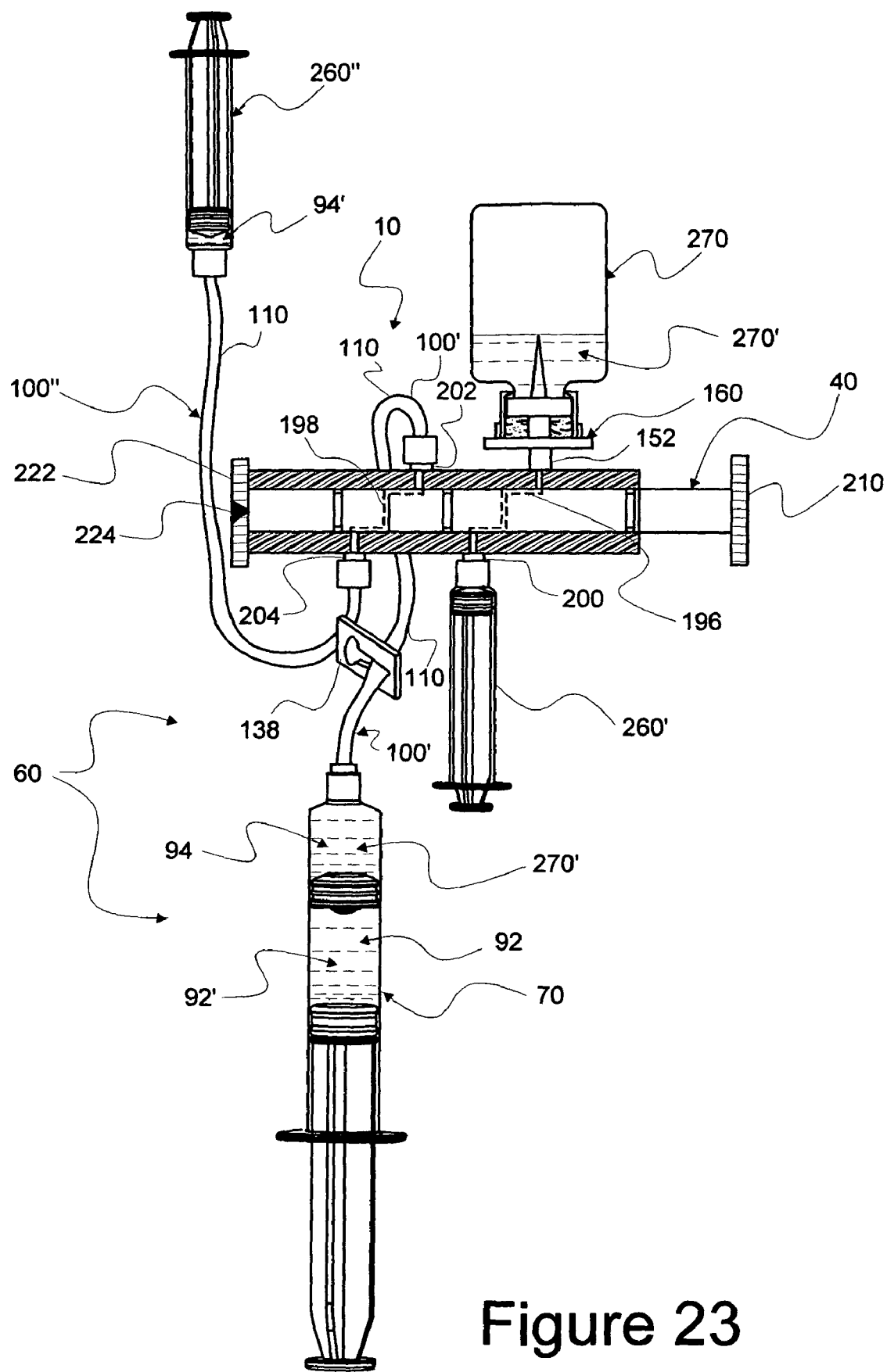
FIG. 23 is a schematic diagram of a step following the step characterized in FIG. 22 wherein a pre-flush tube of a multi-chamber-pre-flush syringe configuration is clamped and occluded preparatory to removing the configuration from the valve assembly.

As seen in FIG. 23, a slider clamp 138 is disposed about tube 110 of tube set 100' to occlude associated tube 100 and capture medicine 270' inferiorly disposed relative to slide clamp 138. With added safety then, tube set 100' may be removed from port 202. Port 202 should there after be capped. Other than multi-chamber-pre-flush syringe configuration 60, all parts used in acquisition of medicine 270' from vial 270 should be carefully and properly disposed of while being maintained in such a sealed state. Multi-chamber-pre-flush syringe configuration 60 should be capped and delivered to a site of use as seen in FIGS. 16 and 17, and as disclosed in detail, supra.

The invention may be embodied in other specific forms without departing from the spirit or essential characteristics thereof. The present embodiment is therefore to be considered in all rests as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A safety valve apparatus and a multi-chamber dispensing syringe assembly combination for transferring a volume of hazardous fluid from a first source containing the hazardous fluid to the multi-chamber dispensing syringe assembly the combination comprising:
   the safety valve apparatus comprising a hermetically sealed valve assembly comprising a plurality of sealable exterior access ports;
   the multi-chamber dispensing syringe assembly comprising a multi-chamber syringe and a pre-flush tube subassembly affixed to a distal end of the multi-chamber syringe, the multi-chamber syringe including a barrel which is divided into a proximal chamber and a distal chamber such that fluid in the proximal chamber is kept separate from fluid in the distal chamber until fluid in the distal chamber is dispensed from the syringe, the multi-chamber dispensing syringe assembly being sealably, but releasably affixed via the pre-flush tube subassembly to a first port from the plurality of sealable exterior access ports;
   the pre-flush tube subassembly comprising an elongated tube having a releasable, sealing connector, disposed at a distal end thereof, by which the multi-chamber dispensing syringe assembly is affixed to the first port;
   the proximal chamber of the multi-chamber syringe being filled with liquid to cleanse the sealing connector as fluid is dispensed from the proximal chamber;
   the first source comprising the hazardous fluid being securely and sealably affixed to a second port from the plurality of sealable exterior access ports;
   a second source, comprising a flush liquid, affixed to a third port from the plurality of sealable exterior access ports;
   the hermetically sealed valve assembly further comprising a structure which is displaceable to at least two states where each state provides at least one isolated internal pathway;
   in a first state, the hermetically sealed valve assembly comprises a first isolated internal pathway which allows fluid to flow between the first and second ports, whereby the hazardous fluid is drawn from the first source through the elongated tube and into the distal chamber of the multi-chamber syringe;
   in a second state, the hermetically sealed valve assembly comprises a second isolated internal pathway which allows fluid to flow between the first and third ports, whereby the flush liquid is drawn from the second source through the first port to substantially fill the elongated tube after the hazardous fluid is drawn from the first source into the distal chamber of the multi-chamber syringe, thereby cleansing the first port of the hazardous fluid; and
   the pre-flush tube subassembly further comprising a clamp disposed about the elongated tube for selectively clamping the elongated tube closed after the flush liquid is drawn into the elongated tube to trap the hazardous fluid between the clamp and the proximal chamber and provide a flushed connection at the first port.

2. A safety valve apparatus and a multi-chamber dispensing syringe assembly combination according to claim 1 wherein the hermetically sealed valve assembly comprises visible exterior indicia which communicates the current state of the hermetically sealed valve assembly to a user.

3. An assembly comprising:
   a valve;
   a hazardous fluid source in fluid communication with the valve, the hazardous fluid source including hazardous medicine;
   a flush liquid source in fluid communication with the valve; and
   a syringe in fluid communication with the valve, the syringe including a distal chamber and a proximal chamber separated by a valved stopper, the syringe being configured to sequentially dispense the contents of the distal chamber and the proximal chamber;

wherein the valve moves between a first state where the syringe is in fluid communication with the hazardous fluid source and a second state where the syringe is in fluid communication with the flush liquid source.

4. The assembly of claim 3 comprising a venting filter positioned between the hazardous fluid source and the valve, the venting filter being configured to allow air from an ambient environment to pass through the venting filter to the hazardous fluid source and prevent the hazardous fluid from escaping into the ambient environment.

5. The assembly of claim 3 wherein the syringe is a delivery syringe, the assembly comprising a first syringe which is in fluid communication with the valve, and wherein the valve moves between one state where the first syringe is in fluid communication with the hazardous fluid source, the first state where the first syringe includes the hazardous fluid and is in fluid communication with the delivery syringe, and the second state where the delivery syringe is in fluid communication with the flush liquid source.

6. The assembly of claim 3 comprising an occluding device positioned between the syringe and the valve, the occluding device being configured to occlude fluid flow between the syringe and the valve.

7. The assembly of claim 6 wherein the occluding device includes a clamp that occludes a tube between the syringe and the valve.

8. The assembly of claim 3 wherein the proximal chamber of the syringe is pre-filled with a flush liquid before the syringe is in fluid communication with the valve.

9. The assembly of claim 3 wherein the hazardous fluid source includes a vial containing a hazardous drug.

10. An assembly comprising:
a valve;
a hazardous fluid source in fluid communication with the valve, the hazardous fluid source including hazardous medicine;
a flush liquid source in fluid communication with the valve; and
a syringe in fluid communication with the valve, the syringe including a distal chamber and a proximal chamber separated by a stopper, the syringe being configured to sequentially dispense the contents of the distal chamber and the proximal chamber;
wherein the valve moves between a first state where the syringe is in fluid communication with the hazardous fluid source and a second state where the syringe is in fluid communication with the flush liquid source; and
wherein the proximal chamber of the syringe is pre-filled with a flush liquid before the syringe is in fluid communication with the valve.

11. The assembly of claim 10 comprising a venting filter positioned between the hazardous fluid source and the valve, the venting filter being configured to allow air from an ambient environment to pass through the venting filter to the hazardous fluid source and prevent the hazardous fluid from escaping into the ambient environment.

12. The assembly of claim 10 wherein the syringe is a delivery syringe, the assembly comprising a first syringe which is in fluid communication with the valve, and wherein the valve moves between one state where the first syringe is in fluid communication with the hazardous fluid source, the first state where the first syringe includes the hazardous fluid and is in fluid communication with the delivery syringe, and the second state where the delivery syringe is in fluid communication with the flush liquid source.

13. The assembly of claim 10 comprising an occluding device positioned between the syringe and the valve, the occluding device being configured to occlude fluid flow between the syringe and the valve.

14. The assembly of claim 13 wherein the occluding device includes a clamp that occludes a tube between the syringe and the valve.

15. The assembly of claim 10 wherein the proximal chamber of the syringe is pre-filled with saline solution.

16. An assembly comprising:
a valve;
a hazardous fluid source in fluid communication with the valve, the hazardous fluid source including hazardous medicine;
a flush liquid source in fluid communication with the valve;
a first syringe in fluid communication with the valve; and
a multi-chamber syringe in fluid communication with the valve, the multi-chamber syringe including a distal chamber and a proximal chamber, the syringe being configured to sequentially dispense the contents of the distal chamber and the proximal chamber;
wherein the valve controls fluid communication between each one of the hazardous fluid source, the flush liquid source, the first syringe, and the multi-chamber syringe and each one of the remaining ones of the hazardous fluid source, the flush liquid source, the first syringe, and the multi-chamber syringe; and
wherein the valve moves between a first state where the first syringe is in fluid communication with the hazardous fluid source, a second state where the first syringe is in fluid communication with the multi-chamber syringe, and a third state where the multi-chamber syringe is in fluid communication with the flush liquid source.

17. The assembly of claim 16 comprising a venting filter positioned between the hazardous fluid source and the valve, the venting filter being configured to allow air from an ambient environment to pass through the venting filter to the hazardous fluid source and prevent the hazardous fluid from escaping into the ambient environment.

18. The assembly of claim 16 comprising an occluding device positioned between the multi-chamber syringe and the valve, the occluding device being configured to occlude fluid flow between the multi-chamber syringe and the valve.

19. The assembly of claim 18 wherein the occluding device includes a clamp that occludes a tube between the multi-chamber syringe and the valve.

20. The assembly of claim 16 wherein the proximal chamber of the multi-chamber syringe is pre-filled with a flush liquid before the multi-chamber syringe is in fluid communication with the valve.

21. The assembly of claim 16 wherein the hazardous fluid source includes a vial containing a hazardous drug.

22. The assembly of claim 16 wherein the first syringe is a measuring syringe sized to accurately measure small volumes of the hazardous fluid.

23. The assembly of claim 16 wherein the multi-chamber syringe is in fluid communication with the flush liquid source when the valve is in the first state.

* * * * *